US 6,599,406 B1

(12) United States Patent
Kawanaka et al.

(10) Patent No.: US 6,599,406 B1
(45) Date of Patent: Jul. 29, 2003

(54) CONCENTRATION MEASURING APPARATUS, TEST STRIP FOR THE CONCENTRATION MEASURING APPARATUS, BIOSENSOR SYSTEM AND METHOD FOR FORMING TERMINAL ON THE TEST STRIP

(75) Inventors: Shoji Kawanaka, Kyoto (JP); Yoshinobu Tokuno, Takamatsu (JP); Kohei Ishida, Kyoto (JP)

(73) Assignees: Kyoto Daiichi Kagaku Co., Ltd., Kyoto (JP); Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/463,179

(22) PCT Filed: Jul. 15, 1998

(86) PCT No.: PCT/JP98/03170
§ 371 (c)(1),
(2), (4) Date: Jan. 21, 2000

(87) PCT Pub. No.: WO99/05516
PCT Pub. Date: Feb. 4, 1999

(30) Foreign Application Priority Data

Jul. 22, 1997 (JP) ............................................. 9-195866

(51) Int. Cl.$^7$ ............................................. G01N 27/327
(52) U.S. Cl. .................. 204/403.02; 204/401; 204/406; 422/82.01
(58) Field of Search ................................. 204/403, 401, 204/406, 416, 403.01, 403.04, 403.02, 403.1; 422/82.01, 82.02, 82.03

(56) References Cited

U.S. PATENT DOCUMENTS

| | | | |
|---|---|---|---|
| 4,714,874 A | * 12/1987 | Morris et al. ................ | 324/444 |
| 5,320,732 A | 6/1994 | Nankai et al. | |
| 5,384,028 A | * 1/1995 | Ito .............................. | 204/403 |
| 5,438,271 A | * 8/1995 | White et al. ................. | 324/444 |
| 5,720,862 A | 2/1998 | Hamamoto et al. | |
| 6,066,243 A | * 5/2000 | Anderson et al. ........... | 204/403 |

FOREIGN PATENT DOCUMENTS

| | | |
|---|---|---|
| EP | 0471986 A2 | 2/1992 |
| JP | 61-500508 | 3/1986 |
| JP | 63- 61157 | 3/1988 |
| JP | 4-357449 | 12/1992 |
| JP | 4-357452 | 12/1992 |
| JP | 8- 94571 | 4/1996 |
| JP | 8-504953 | 5/1996 |
| JP | 8-278276 | 10/1996 |
| JP | 9- 43189 | 2/1997 |
| JP | 9-159644 | 6/1997 |
| JP | 10-332626 A | 12/1998 |
| WO | 85 02257 | 5/1985 |
| WO | 94 29705 | 12/1994 |

* cited by examiner

Primary Examiner—Robert J. Warden, Sr.
Assistant Examiner—Kaj K. Olsen
(74) Attorney, Agent, or Firm—Birch, Stewart, Kolasch & Birch, LLP

(57) ABSTRACT

The present invention is to provide a concentration measuring apparatus, a test strip for the concentration measuring apparatus, a biosensor system and a method for forming terminals of the test strip, whereby a component to be measured can be measured by the test strip fit to the target component to be measured. A type judgement electrode is provided separately from a positive electrode and a negative electrode in a measuring apparatus so as to judge the type of a set test strip with the measuring apparatus. Thus only when a test strip matching the measuring apparatus is set, the type judgement electrode is electrically connected to a terminal of the set test strip, enabling the measuring apparatus to measure a component to be measured in a liquid test sample. A measuring apparatus detects a calibration curve information selection change for selecting a calibration curve information corresponding to a production lot of the set test strip thereby to compensate for an error in a measured concentration value of the component.

52 Claims, 16 Drawing Sheets

PRIOR ART

PRIOR ART

CONCENTRATION MEASURING APPARATUS, TEST STRIP FOR THE CONCENTRATION MEASURING APPARATUS, BIOSENSOR SYSTEM AND METHOD FOR FORMING TERMINAL ON THE TEST STRIP

TECHNICAL FIELD

The present invention relates to a concentration measuring apparatus for measuring a concentration of a specific component in a solution with the use of a socalled biosensor, a test strip to be used in the concentration measuring apparatus, a biosensor system using the concentration measuring apparatus and the test strip, and a method for forming a terminal on the test strip. The solution to be measured is specifically humor, e.g., blood, blood plasma, urine, saliva, etc. Blood is particularly often used.

BACKGROUND ART

Measuring apparatuses using a so-called biosensor are now in practical use for quantitatively detecting a specific component in humors of living bodies such as blood, urine or the like. In the measuring apparatus of the type, a compact and disposable test strip is fitted as the biosensor, and for instance, blood is dropped on the test strip, thereby to measure a concentration of glucose, lactic acid, cholesterol or the like in the blood.

The aforementioned method and a structure of the test strip for the concentration measurement are disclosed, for example, in the published specification of Japanese Patent Laid-Open Publication No. 4-357452. The test strip of this prior art is constructed as shown in FIG. 33. Specifically, a conductive carbon paste or the like is screen printed on a sheet of a strip of an insulating base material 2 thereby to form terminals 3, 4 adjacent to each other at one end part in a longitudinal direction of the base material 2. The terminals 3, 4 are extended in the longitudinal direction to form a measuring electrode 5 and a counter electrode 6 facing the measuring electrode 5 at the other end part of the base material 2. An insulating layer is formed on the insulating base material except for portions on the terminals 3, 4, the measuring electrode 5, and the counter electrode 6. A reaction reagent (not shown) composed of an enzyme, a mediator, etc. corresponding to a component to be measured is applied on the measuring electrode 5 and the counter electrode 6. A cover 8 is fitted via a spacer 7 over the base material 2 except the terminals 3, 4. A test strip 1 of FIG. 34 is thus obtained. A projection 10 is formed so as to prevent the test strip 1 from being set to a measuring apparatus in a wrong direction.

As is revealed, e.g., in the prior art No. 4-357452, the test strip 1 is set to a measuring apparatus 20 by being inserted from the side of the terminals 3, 4 to a setting part 21 of a card-shaped measuring apparatus 20 as shown in FIG. 35. A display part 22 is provided at a surface of the measuring apparatus 20 to display measurement results. The setting part 21 of the conventional measuring apparatus 20 has a positive and a negative electrodes to be electrically connected to the terminals 3, 4 of the test strip 1 when the test strip 1 is set to the measuring apparatus 20.

After the test strip 1 is set to the measuring apparatus 20, as is clear from the same prior art No. 4-357452, for instance, blood is spotted on the other end part of the test strip 1, which is aspirated by a capillary action to a space 9 formed in the spacer 7, reaches the reaction agent applied on the measuring electrode 5 and counter electrode 6 and reacts with the reaction reagent. A voltage is impressed then to the terminals 3, 4 of the test strip 1 from the measuring apparatus 20, whereby a reaction product through a reaction with the enzyme is oxidized. A current generated in this oxidation is measured at the measuring apparatus 20. The measured oxidation current is converted to a concentration of the specific component to be measured.

The reaction reagent used is, e.g., one that includes glucose oxidase as the enzyme when glucose in the solution is to be measured, or that includes lactate oxidase, cholesterol oxidase when lactic acid, cholesterol in the solution is to be measured, as disclosed in a published specification of Japanese Patent Laid-Open No. 8-278276.

As is apparent from the above description, the test strip corresponding to each component to be measured can be obtained by replacing the enzyme contained in the reaction reagent without changing a basic of the test strip 1. In other words, the structure of test strips can be made common in various kinds of components to be measured, and the measuring apparatus and manufacturing facility for the test strips can be shared, with the effect of a cost reduction for manufacturing the measuring apparatus and test strips. Although it is ideal that the test strips for corresponding components are demanded the same degree, practically, test strips for glucose are required most, while those for lactic acid or cholesterol are less required. If the test strips are constituted in the same structure, in the aforementioned irregular demand, the test strip for the irregular demand can be obtained simply only by changing the reaction reagent.

However, if in the common structure of test strips, it becomes difficult to distinguish the test strips, for example, between glucose test strips and lactic acid test strips. It may happen that the lactic acid test strip is inadvertently set to the measuring apparatus even though a concentration of glucose is necessary. Thus, an incorrect result is obtained.

The present invention is devised to solve the above-described inconvenience and has for its object to provide a concentration measuring apparatus, a test strip for use in the measuring apparatus, a biosensor system, and a method for forming terminals on the test strip whereby a target component is measured with the test strip fit thereto.

DISCLOSURE OF INVENTION

In accomplishing these and other aspects, according to a first aspect of the present invention, there is provided a concentration measuring apparatus to which a test strip is set, the test strip including on a base material a reaction reagent which is to react with a liquid test sample, a positive terminal, and a negative terminal, the terminals electrically detecting a concentration of a specific component in the liquid test sample based on the reaction of the reaction reagent, the concentration measuring apparatus comprising a positive electrode and a negative electrode to be electrically connected respectively to the positive terminal and the negative terminal of the test strip, thereby operating the concentration of the specific component in the liquid test sample via the positive electrode and the negative electrode, the concentration measuring apparatus further comprising a type judgement electrode for judging a type of the test strip set to the concentration measuring apparatus with the type judgement electrode provided separately from the positive electrode and negative electrode.

As is fully described above, in the concentration measuring apparatus of the first aspect of the present invention, the type judgement electrode is added separately to the positive electrode and negative electrode. Thus, the specific component to be measured can be measured by the test strip which is appropriate to measure the specific component with the utilization of the type judgement electrode.

According to a second aspect of the present invention, the concentration measuring apparatus may further comprises a first identification device for feeding information corresponding to the test strip for the liquid test sample capable of measuring the specific component based on a fact that the type judgement electrode is connected with the positive electrode only when the test strip capable of measuring the specific component is set to the concentration measuring apparatus, and a second identification device for identifying the test strip based on the information fed from the first identification device.

According to the concentration measuring apparatus of the second aspect of the present invention, the first and second identification devices are provided further in the measuring apparatus of the first embodiment, which exhibits the following effects. When the test strip capable of measuring the component to be measured is set, the type judgement electrode and positive electrode are connected with each other, with information of the type of the set test strip being sent out from the first identification device. The second identification device recognizes based on the type information that an appropriate test strip to the measuring apparatus is set. The component to be measured can accordingly be measured by the appropriate test strip to the measuring apparatus.

According to a third aspect of the present invention, the concentration measuring apparatus may comprises switches for connecting or disconnecting the type judgement electrode and positive electrode, and for connecting or disconnecting the type judgement electrode and negative electrode, and an identification device for identifying that the test strip for the liquid test sample capable of measuring the specific component is set to the concentration measuring apparatus on the basis of information obtained from a detecting part of the positive electrode consequent to turning ON/OFF of each of switches.

According to the third aspect of the present invention, the concentration measuring apparatus of the first embodiment is further provided with the switches and the identification device, which exhibits the following effects. The identification device can judge whether or not the test strip conforming to the measuring apparatus is set based on the information of the detecting part of the positive electrode consequent to the turning ON/OFF of the switches. Therefore, the component to be measured can be measured by the appropriate test strip to the measuring apparatus.

According to a fourth aspect of the present invention, the concentration measuring apparatus may comprises a potential judge device connected to the type judgement electrode which judges whether or not the type judgement electrode becomes an appropriate test strip set potential which is a potential generated at the type judgement electrode when the test strip for the liquid test sample capable of measuring the specific component is set to the concentration measuring apparatus.

According to the fourth aspect of the present invention, the potential judge device is included in the concentration measuring apparatus of the first embodiment. The potential judge device detects the potential of the type judgement electrode thereby to judge whether or not the potential is the appropriate test strip set potential. When the potential is the appropriate test strip set potential, the potential judge device judges that the test strip fit to the concentration measuring apparatus is set.

Accordingly, the component to be measured can be measured by the test strip conforming to the measuring apparatus.

According to a fifth aspect of the present invention, the concentration measuring apparatus may comprises a change judge device connected to the type judgement electrode which judges whether or not a potential change at the type judgement electrode corresponds to an appropriate test strip set change which is a change generated at the type judgement electrode when the test strip for the liquid test sample capable of measuring the specific component is set to the concentration measuring apparatus.

The concentration measuring apparatus of the fifth aspect has the change judge device added to the concentration measuring apparatus of the first embodiment. More specifically, the change judge device detects the potential change at the type judgement electrode when the test strip is set to the measuring apparatus, thereby judging whether or not the potential change corresponds to the appropriate test strip set change. If the potential change is the appropriate test strip set change, the change judge device judges that the test strip suitable to the measuring apparatus is set. The component can hence be measured by the test strip matching the measuring apparatus.

According to a sixth aspect of the present invention, there is provided a test strip to be set to the concentration measuring apparatus in the second aspect of the present invention, which comprises a type judgement terminal which is to be electrically connected to the type judgement electrode and positive electrode, thereby letting the first identification device of the concentration measuring apparatus send out the information corresponding to the test strip for the liquid test sample capable of measuring the specific component.

According to the sixth aspect of the present invention, the test strip set to the concentration measuring apparatus of the second aspect has the type judgement terminal. Since the information that the test strip is fit to the measuring apparatus is sent out from the first identification device, the test strip enables the measuring apparatus to judge that the test strip appropriate to the measuring apparatus is set.

According to a seventh aspect of the present invention, there is provided a test strip to be set to the concentration measuring apparatus in the fourth aspect of the present invention, which is characterized by comprises a type judgement terminal which is to be electrically connected to the type judgement electrode and letting the potential judge device judge that the potential at the type judgement electrode is the appropriate test strip set potential.

In the seventh aspect of the present invention, the test strip is set to the concentration measuring apparatus of the fourth aspect, which is equipped with the type judgement terminal. The test strip enables the potential judge device to judge that the potential at the type judgement electrode is the appropriate test strip set potential. The test strip of the seventh aspect enables the measuring apparatus to judge that the appropriate test strip is set to the measuring apparatus.

According to a eighth aspect of the present invention, there is provided a test strip to be set to the concentration measuring apparatus in the fifth aspect of he present invention, which comprises type judgement terminal to be electrically connected to the type judgement electrode and letting the change judge device judge that the potential change at the type judgement electrode corresponds to the appropriate test strip set change.

According to the eighth aspect, the test strip is set to the measuring apparatus of the fifth aspect and equipped with the type judgement terminal. The change judge device can consequently judge that the potential of the type judgement electrode shows the change by an appropriate test strip. The test strip enables the measuring apparatus to judge that the appropriate test strip is set.

According to a ninth aspect of the present invention, there is provided a biosensor system which comprises a first concentration measuring apparatus comprising the concentration measuring apparatus according to the second aspect wherein the positive electrode, the type judgement electrode, and the negative electrode are arranged in this order in a direction orthogonal to a set direction of a test strip;

a first test strip comprising the test strip according to the sixth aspect to be set to the first concentration measuring apparatus, which includes first terminals to be electrically connected to the positive electrode and the type judgement electrode, and a second terminal to be electrically connected to the negative electrode;

a second concentration measuring apparatus comprising the concentration measuring apparatus according to the second aspect wherein the positive electrode, the negative electrode, and the type judgement electrode are arranged in this order in the orthogonal direction; and a second test strip comprising the test strip according to the sixth aspect to be set to the second concentration measuring apparatus which includes a first terminal to be electrically connected to the positive electrode and type judgement electrode and a second terminal to be electrically connected to the negative electrode, said biosensor system so constituted that a concentration of the specific component cannot be operated if the first test strip is set to the second concentration measuring apparatus, and if the second test strip is set to the first concentration measuring apparatus.

The biosensor system in accordance with the ninth aspect of the present invention is constituted so that only one kind of the test strip conforms to one kind of the concentration measuring apparatus, making it impossible to share test strips and concentration measuring apparatuses among different kinds.

According to a tenth aspect of the present invention, in the concentration measuring apparatus of the fifth aspect, the change judge device may stores a plurality of calibration curve information for compensating for an error in concentration measurement of the specific component in the liquid test sample, detects a calibration curve information selection change at the type judgement electrode so as to select a required calibration curve information among the plurality of calibration curve information in place of judging the presence/absence of the appropriate test strip set change at the type judgement electrode when the concentration measuring apparatus can measure the concentration of the only one specific component and the test strip having a reaction reagent which is to react to the specific component and capable of measuring the concentration of the specific component by the concentration measuring apparatus is set to the concentration measuring apparatus, and compensates for the error based on the calibration curve information selected in accordance with the detected calibration curve information selection change.

According to the concentration measuring apparatus in the tenth aspect, the calibration curve information selection change is detected, instead of detecting the presence/absence of the appropriate test strip set change in the measuring apparatus of the fifth aspect. The calibration curve information can be selected on the basis of the above detection, and the measurement error can be compensated for by the selected calibration curve information. Accordingly, the concentration of the specific component can be obtained with higher accuracy.

According to a 11th aspect of the present invention, in the concentration measuring apparatus of the fifth aspect, the change judge device may stores a plurality of calibration curve information for compensating for an error in concentration measurement of the specific component in the liquid test sample, selects a required calibration curve information among the plurality of calibration curve information on the basis of a calibration curve information selection change included in the appropriate test strip set change at the type judgement electrode as well as judges a type of the test strip on the basis of the appropriate test strip set change at the type judgement electrode, and compensates for the error based on the selected calibration curve information.

According to the 11th aspect, in the concentration measuring apparatus of the fifth aspect, the calibration curve information selection change is detected in addition to the detection of the presence/absence of the appropriate test strip set change, whereby the calibration curve information corresponding to the detected type of the test strip set to the measuring apparatus and the production lot of the test strip can be selected.

According to a 12th aspect of the present invention, there is provided a test strip to be set to the concentration measuring apparatus of the 10th aspect, which has a type judgement terminal to be electrically connected to the type judgement electrode and letting the change judge device detect the calibration curve information selection change for selecting the required calibration curve information among the plurality of calibration curve information on the basis of the potential at the type judgement electrode.

According to the 12th aspect of the present invention, the test strip is set to the concentration measuring apparatus of the 10th aspect. The test strip is provided with the type judgement terminal for detecting the calibration curve information selection change, thus enabling the change judge device to select the calibration curve information.

According to a 13th aspect of the present invention, there is provided a test strip to be set to the concentration measuring apparatus of the 11th aspect, which has a type judgement terminal to be electrically connected to the type judgement electrode and letting the change judge device judge that the potential change at the type judgement electrode is the appropriate test strip set change for judging the type of the test strip and also letting the change judge device detect the calibration curve selection information change for selecting the required calibration curve information among the plurality of calibration curve information.

The test strip of the 13th aspect is set to the concentration measuring apparatus of the 10th aspect, which includes the type judgement terminal for detecting the calibration curve information selection change as well as the presence/absence of the appropriate test strip set change. Thus, the test strip of the 13th aspect enables the change judge device to judge the kind of the specific component measurable by the test strip set to the measuring apparatus and moreover, select the calibration curve information.

According to a 14th aspect of the present invention, there is provided a method for manufacturing the test strip of the 12th and 13th aspects, which comprises:

applying the reaction reagent on the base material of the test strip;

dropping a standard solution having the specific component of which a concentration is known to the applied reaction reagent;

selecting the calibration curve information compensating for an error between a detected concentration based on the reaction and the known concentration of the specific component; and forming the type judgement terminal so that the calibration curve information selection change indicating at least the selected calibration curve information is generated at the type judgement terminal.

In the method for forming the terminals of the test strip according to the 14th aspect, after the calibration curve information is selected, the type judgement terminal is formed to the test strip of the 12th, 13th aspect so that the calibration curve information selection change is brought about.

BRIEF DESCRIPTION OF DRAWING

These and other aspects and features of the present invention will become clear from the following description taken in conjunction with the preferred embodiments thereof with. reference to the accompanying drawings, in which.

BEST MODE FOR CARRYING OUT THE INVENTION

Figure 1:
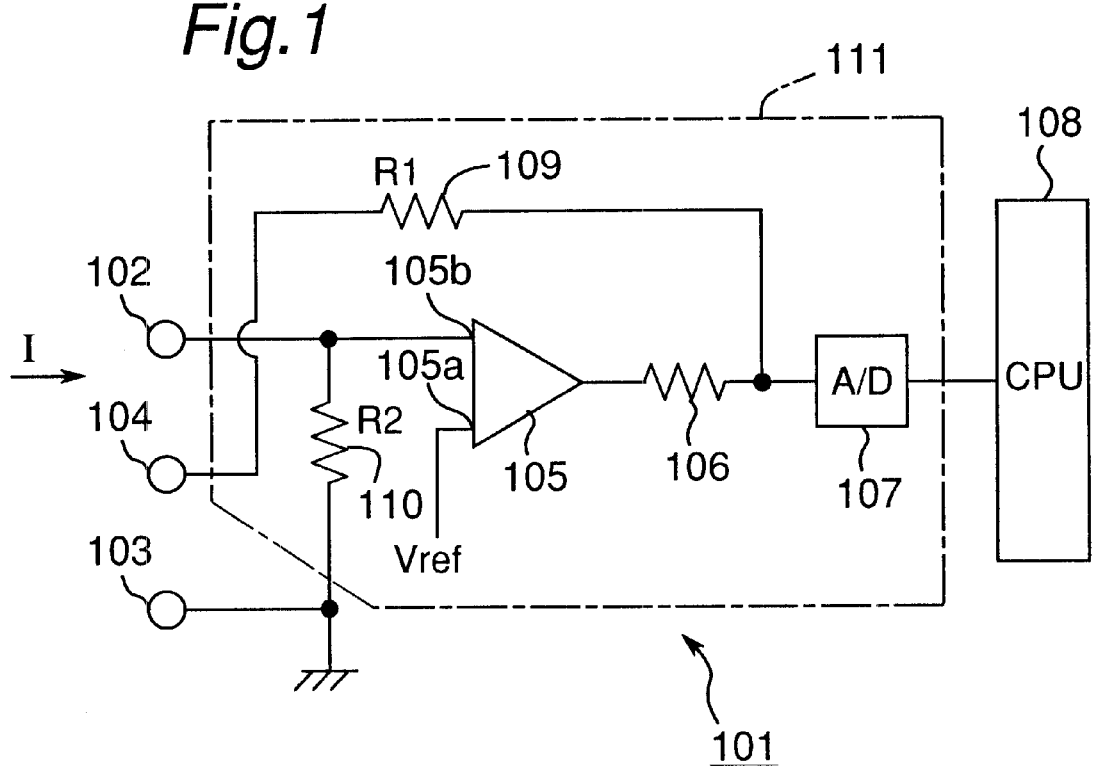
FIG. 1 is a structural diagram of a concentration measuring apparatus according to a first embodiment of the present invention.

A concentration measuring apparatus, a test strip for use in the concentration measuring apparatus, a biosensor system equipped with the concentration measuring apparatus and test strip, and a method for forming terminals on the test strip according to preferred embodiments of the present invention will be described with reference to the drawings. In the embodiments, a liquid test sample including a component to be measured is, e.g., humor of living bodies such as blood, blood plasma, urine and salivary juice, especially blood. However, the liquid test sample is not limited to the above and includes liquids including components measurable by a reaction reagent. The component to be measured is glucose, and lactic acid in the embodiments, but not restricted to these kinds of stuff.

In the drawings, parts functioning the same or similarly are denoted by the same reference numerals and the description thereof will not be duplicated except what is to be particularly noted.

First Embodiment

Figure 2:
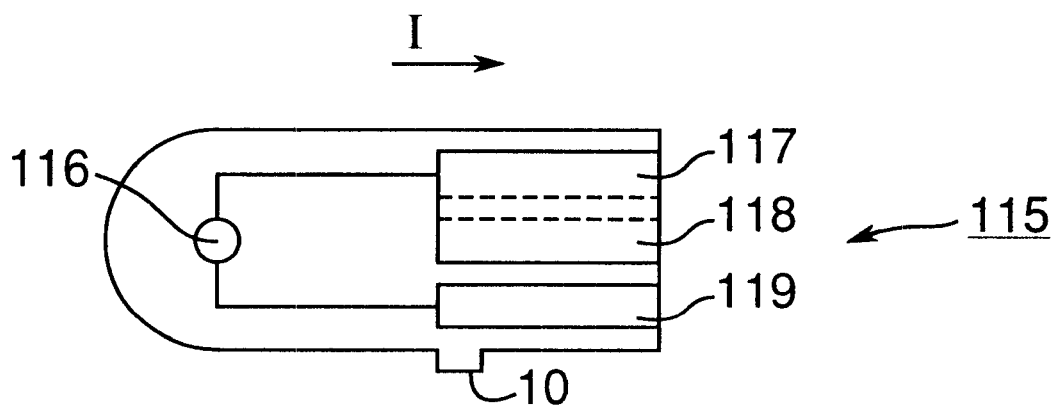
FIG. 2 is a plan view of a test strip to be set to the concentration measuring apparatus and fit to the concentration measuring apparatus of FIG. 1.
Figure 3:
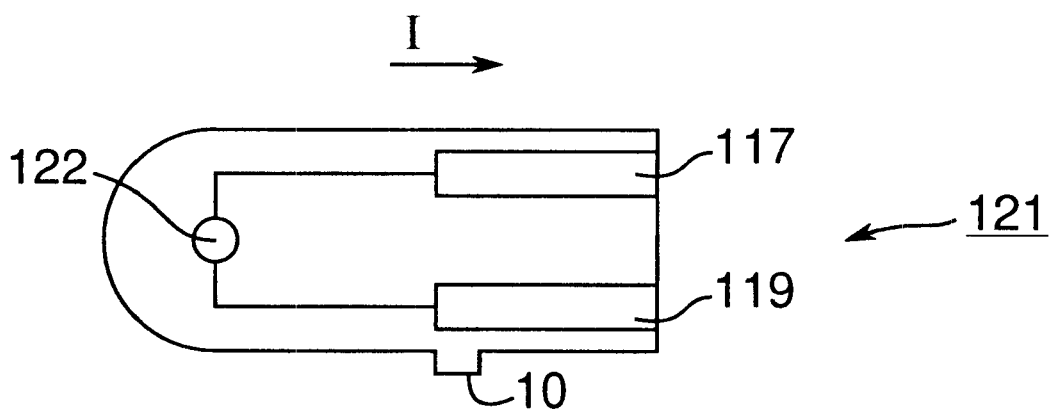
FIG. 3 is a plan view of a test strip to be set to the concentration measuring apparatus and not fit to the concentration measuring apparatus of FIG. 1.

A concentration measuring apparatus and a test strip for the concentration measuring apparatus according to a first embodiment of the present invention are shown in FIGS. 1 through 3. An example functioning as the first identification device described in the foregoing "Disclosure Of Invention" is a circuit part 111 to be described later which comprises an amplifier 105, an A/D converter 107, a connecting line including an R1 resistor 109, an R2 resistor 110, and a resistor 106. On the other hand, an example of the second identification device described in the "Disclosure Of Invention" is a CPU 108 to be described later. Further, a digital value sent out from the A/D converter 107 to be described later corresponds to an embodiment of "the information corresponding to the test strip capable of measuring the specific component of the liquid test sample" in the "Disclosure Of Invention".

A concentration measuring apparatus 101 shown in FIG. 1 will be described first. The concentration measuring apparatus 101 has a type judgement electrode 104 in addition to a positive electrode 102 and a negative electrode 103 provided in the conventional measuring apparatus alike. The type judgement electrode 104 is a electrode for judging whether or not a test strip capable of measuring a concentration in the measuring apparatus 101 is set to the measuring apparatus 101. The positive electrode 102, the type judgement electrode 104, and the negative electrode 103 are arranged in this order in a row in a direction orthogonal to a set direction I of the test strip to the measuring apparatus 101, as indicated in FIG. 1. The concentration measuring apparatus 101 includes therein the amplifier 105, the A/D converter 107 connected to an output of the amplifier 105 via the resistor 106, the CPU 108 (central processing unit), the R1 resistor 109, and the R2 resistor 110. An input terminal 105a of the amplifier 105 is connected with a reference voltage source Vref, and the other input terminal 105b of the amplifier 105 is connected with the positive electrode 102. The type judgement electrode 104 is connected to the output of the amplifier 105 via the R1 resistor 109. The negative electrode 103 is grounded and, also a connecting line between the amplifier 105 and positive electrode 102 is grounded via the R2 resistor 110. The CPU 108 controls operations of the concentration measuring apparatus 101, e.g., controls to calculate a concentration of a component to be measured, as well as judges whether or not the test strip capable of measuring the concentration in the measuring apparatus 101 is set to the measuring apparatus 101, in other words, carries out an identification action. That is, the CPU 108 functions as an identification device as well. However, an identification device performing only the identification action may be provided separately from the CPU 108. Although the identification action will be detailed later, since the digital values are changed based on whether or not the test strip capable of measuring the concentration at the measuring apparatus 101 is set to the measuring apparatus 101, the CPU 108 determines whether or not the test strip capable of measuring the concentration at the measuring apparatus 101 is set to the measuring apparatus 101 based on a difference of digital values fed from the A/D converter 107.

In an example of the first embodiment, the R1 resistor 109 is 100 kΩ, R2 resistor 110 is 100 kΩ, reference voltage source Vref is 0.5V, and the amplifier 105 has 5V source voltage.

The operation of the concentration measuring apparatus 101 constituted as above will be depicted below. FIGS. 2 and 3 are simplified diagrams of test strips 115, 121 to be set to the concentration measuring apparatus 101. A fundamental structure of each test strip 115, 121 is equal to that of the conventional test strip 1 illustrated in FIGS. 33 and 34. Reference numerals 116, 122 in FIGS. 2 and 3 correspond to the reaction reagent described earlier. The measuring electrode 5 and counter electrode 6 are hidden by the reaction reagents 116, 122, and not shown in the drawings. The reaction reagent that can be measured by the concentration measuring apparatus 101 is applied to the test strip 115, and a component to be measured in the liquid test sample cannot be measured even if the test strip 121 is set to the measuring apparatus 101.

In the test strip 115, a positive terminal 117, a type judgement terminal 118, and a negative terminal 119 are formed in a direction orthogonal to the set direction I of the test strip 115 to the measuring apparatus 101 to be electrically connected to the corresponding positive electrode 102, type judgement electrode 104, and negative electrode 103 of the concentration measuring apparatus 101. The positive terminal 117 and type judgement terminal 118 of the test strip 115 are formed integrally into one terminal, so that the positive terminal 117 and type judgement terminal 118 are electrically connected to the measuring electrode 5, and the negative terminal 119 is electrically connected to the counter electrode 6.

Meanwhile, the test strip 121 has no terminal corresponding to the above type judgement terminal 118, with having only the positive terminal 117 and negative terminal 119. In other words, the test strip 121 is the same as the conventional test strip 1.

When the test strip 115 is set to the concentration measuring apparatus 101, the positive electrode 102 and positive terminal 117, the type judgement electrode 104 and type judgement terminal 118, and the negative electrode 103 and negative terminal 119 are electrically connected with each other respectively. Since the positive terminal 117 and type judgement terminal 118 are integrally formed in the test strip 115, actually, the positive electrode 102 and type judgement electrode 104 are shortcircuited at the concentration measuring apparatus 101.

When the test strip 115 is set as above, a feedback circuit is formed in the amplifier 105 via the R1 resistor 109 because of the shortcircuit between the positive electrode 102 and type judgement electrode 104 of the concentration measuring apparatus 101. As a result, the amplifier 105 outputs a voltage V1 exceeding the reference voltage Vref due to resistances of the R1 resistor 109, R2 resistor 110 and the test strip 115. The A/D converter 107 digitizes the voltage V1 and sends a digital value D1 corresponding to the voltage V1 to the CPU 108.

The CPU 108 has the digital value D1 set beforehand therein. When the digital value D1 is supplied from the A/D converter 107, the CPU 108 judges that the supplied digital value is equal to the set digital value D1, and accordingly detects that the test strip 115 with the reaction reagent 116 which can be measured by the measuring apparatus 101 is set to the measuring apparatus 101. The concentration of the component to be measured is started to be measured.

On the other hand, if a test strip other than the test strip 115, e.g., the test strip 121 is set to the measuring apparatus 101, the positive electrode 102 and type judgement electrode 104 of the measuring apparatus 101 are not shortcircuited because the test strip 121 does not have the type judgement terminal 118. Thus the aforementioned feedback circuit is not formed in the amplifier 105. The input terminal 105b of the amplifier 105 connected to the positive electrode 102 is consequently grounded via the R2 resistor 110. In the absence of the feedback circuit, a potential difference between the input terminal 105b and reference voltage Vref causes the amplifier 105 to output a voltage V2 which is larger than the voltage V1, considerably large as compared with the reference voltage Vref and close to the source voltage of the amplifier 105. The A/D converter 107 digitizes the voltage V2 to a digital value D2 corresponding to the voltage V2 and sends the value D2 to the CPU 108.

The sent digital value D2 is different from the digital value D1, and therefore the CPU 108 detects that the test strip 121 with the reaction reagent 122 which cannot be measured by the measuring apparatus 101 is set to the measuring apparatus 101. The concentration measurement is hence not executed.

The circuit part corresponding to a first identification device 111 is used also to measure the component to be measured of the liquid test sample when the test strip 115 with the reaction reagent 116 measurable by the measuring apparatus 101 is set to the measuring apparatus 101. The measurement operation will be discussed hereinbelow, in which the liquid test sample dropped to the test strip 115 is blood and the component to be measured is glucose, by way of example.

When the test strip 115 is set to the concentration measuring apparatus 101, the feedback circuit is formed in the amplifier 105 because of the shortcircuit of the positive electrode 102 and type judgement electrode 104 of the measuring apparatus 101 as described hereinabove. The reference voltage Vref of the amplifier 105 is impressed to a part of the test strip 115 where the reaction reagent 116 is applied. In the meantime, blood is dropped on the reaction reagent 116. A voltage corresponding to the oxidation current through the reaction between the reaction reagent 116 and blood is output from the amplifier 105 to the A/D converter 107, similar to the prior art. Needless to say, the oxidation current varies in accordance with a concentration of glucose in the dropped blood. The CPU 108 converts the digital value sent from the A/D converter 107 corresponding to the concentration of glucose in the blood to a blood sugar value. The blood sugar value as a measurement result is displayed at the display part 22.

According to the above-described first embodiment, only when the test strip 115 equipped with the reaction reagent 116 measurable by the measuring apparatus 101 is set to the measuring apparatus 101, the measurement operation for the component is carried out. Therefore, incorrect measurements can be avoided even if a test strip designed for measurement of lactic acid is inadvertently set to the measuring apparatus 101 instead of a glucose test strip.

Second Embodiment

A concentration measuring apparatus and a test strip used in the concentration measuring apparatus according to a second embodiment of the present invention are indicated in FIGS. 4–6 and 2. A CPU 134 to be described later corresponds to an embodiment of the identification device described in the "Disclosure Of Invention". At the same time, a digital value output from the A/D converter 107 to be described later is an example of "the information of the detecting part of the positive electrode" in the "Disclosure Of Invention".

Figure 4:
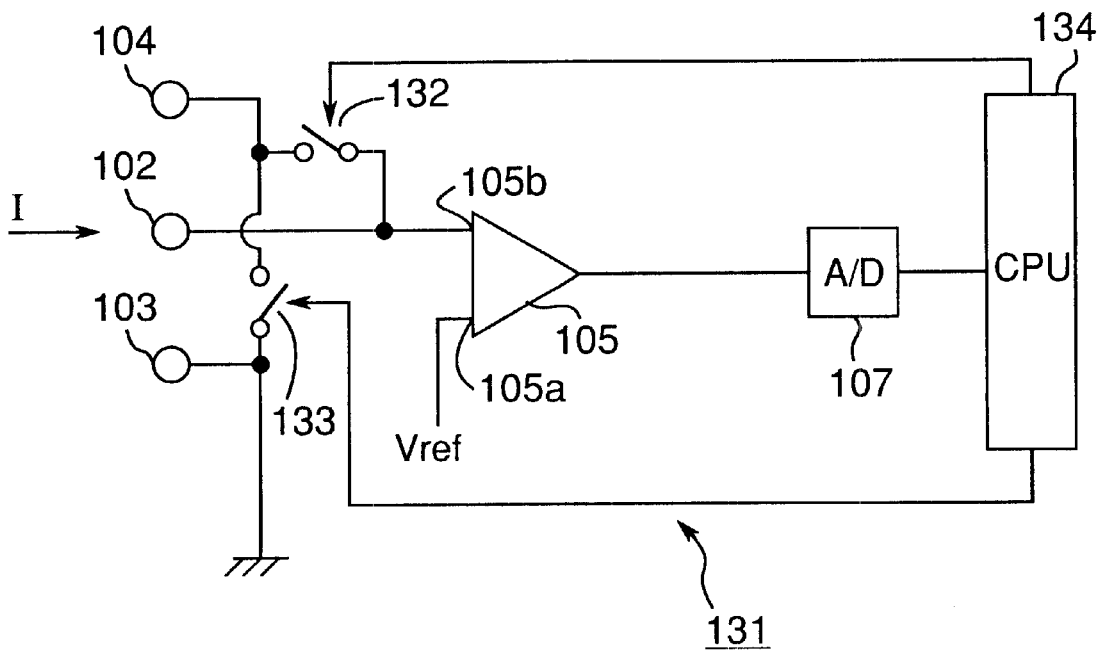
FIG. 4 is a structural diagram of a concentration measuring apparatus according to a second embodiment of the present invention.

A concentration measuring apparatus 131 shown in FIG. 4 will be described. The concentration measuring apparatus 131 alike is provided with the type judgement electrode 104. As indicated in FIG. 4, the type judgement electrode 104, positive electrode 102, and negative electrode 103 are arranged in a row in this order along the direction orthogonal to the set direction I in the concentration measuring apparatus 131. The type judgement electrode 104 in the measuring apparatus 131 is connected to the input terminal 105b of the amplifier 105 via a switch 132 and also grounded via a switch 133. These switches 132, 133 are individually turned ON, OFF under control of a CPU 134. The output of the amplifier 105 is connected to the CPU 134 via the A/D converter 107.

Figure 18:
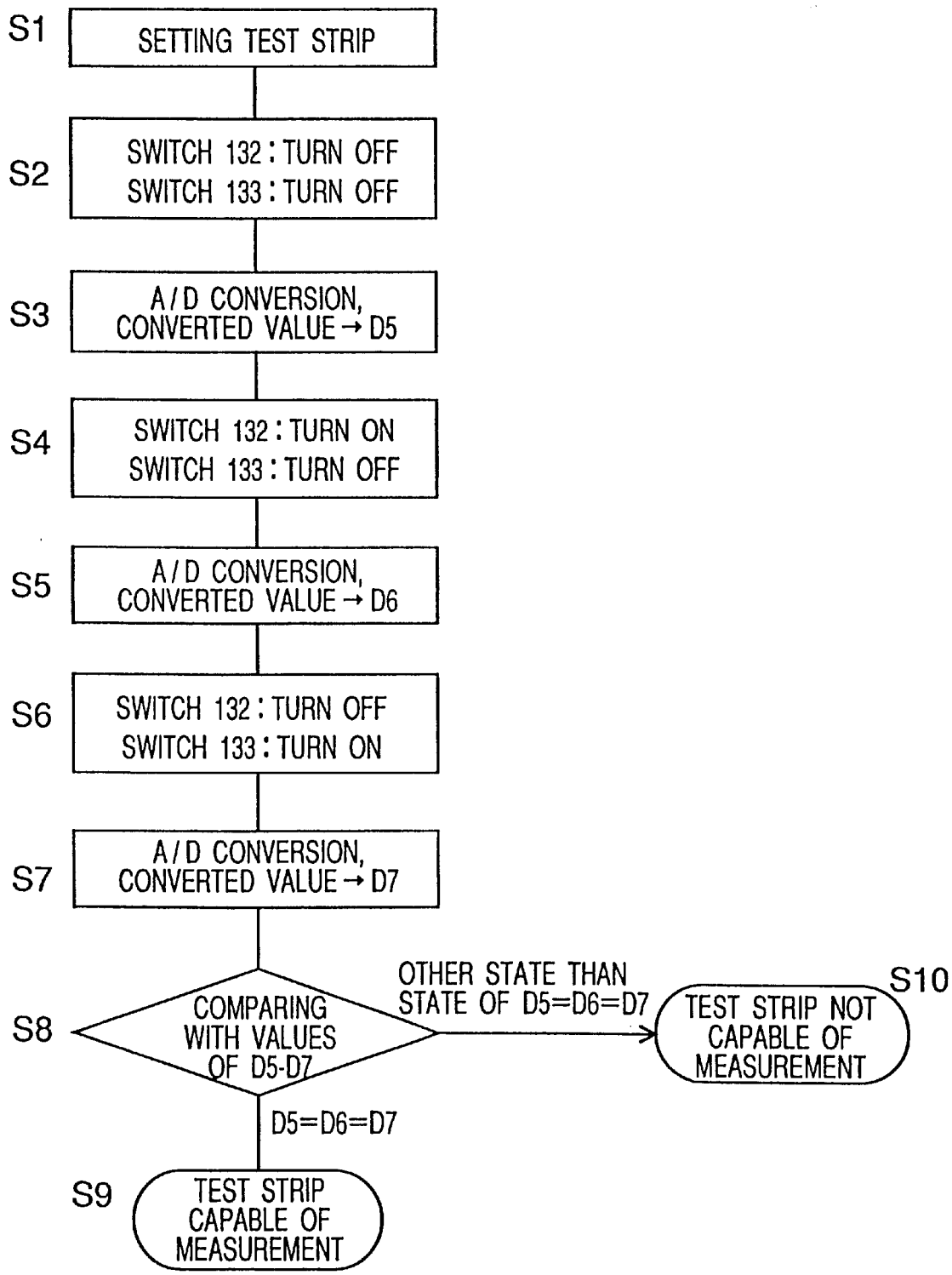
FIG. 18 is a flow chart showing operations of the concentration measuring apparatus of FIG. 4.

The CPU 134 makes control in the following manner to measure the concentration of the component to be measured in the liquid test sample solely when a test strip with a reaction reagent measurable by the measuring apparatus 131 is set to the measuring apparatus 131. Specifically, as shown in FIG. 18, when a test strip is mounted to the measuring apparatus 131 in step 1, the CPU 134 turns OFF both of the switches 132, 133 in step 2 a predetermined time later after the test strip is perfectly set to the apparatus 131. In step 3, a digital value D5 supplied in this state from the A/D converter 107 is stored in the CPU 134 (referred to the operation of the steps 1–3 as "a first operation" hereinafter). A predetermined time later after the digital value D5 is stored, the CPU 134 turns ON the switch 132 and keeps the switch 133 OFF in step 4, and stores a digital value D6 fed in this state from the A/D converter 107 in step 5 (referred to the operation of the steps 4 and 5 as "a second operation"). A redetermined time later after the digital value D6 is stored, the CPU 134 turns OFF the switch 132 and turns ON the switch 133 in step 6. A digital value D7 from the A/D converter 107 is then stored in step 7 (referred to the operation of the steps 6 and 7 as "a third operation"). In step 8, the CPU 134 decides whether or not the digital values D5–D7 are totally equal, and judges that the test strip having the reaction reagent measurable by the measuring apparatus 131 is set to the measuring apparatus 131 only when the digital values D5–D7 are all equal. Then the CPU 134 starts to measure the component in step 9. In other cases than when all of the digital values D5–D7 are equal, in step 10, the CPU 134 judges that the test strip with the reaction reagent not measurable by the measuring apparatus 131 is set to the measuring apparatus 131.

Figure 5:
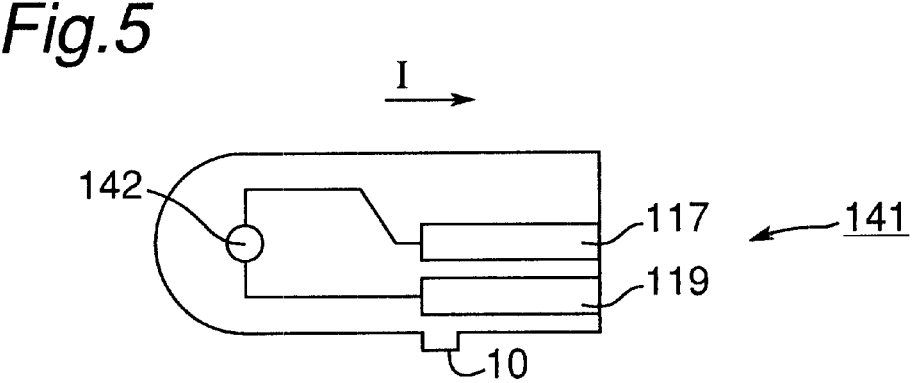
FIG. 5 is a plan view of a test strip to be set to the concentration measuring apparatus and fit to the concentration measuring apparatus of FIG. 4.
Figure 6:
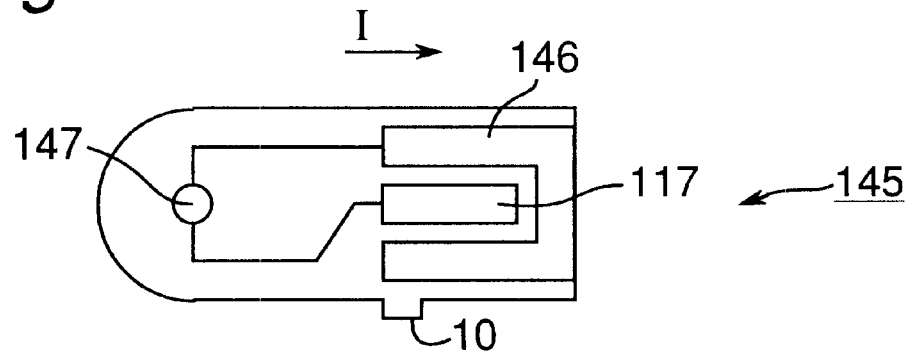
FIG. 6 is a plan view of a test strip to be set to the concentration measuring apparatus and not fit to the concentration measuring apparatus of FIG. 4.

The concentration measuring apparatus 131 of the above constitution operates in a manner as will be described below. In FIGS. 5 and 6, test strips 141, 145 to be set to the concentration measuring apparatus 131 are illustrated in a simplified fashion, which are basically similar structure to the conventional test strip 1 in FIGS. 33 and 34. Reference numerals 142, 147 in FIGS. 5 and 6 correspond to the reaction reagent. Although not shown in the drawings and hidden by the reaction reagents 142, 147, the measuring electrode 5 and counter electrode 6 are arranged. In the test strip 141, the reaction reagent measurable by the measuring apparatus 131 is applied. The component in the liquid test sample cannot be measured even if the test strip 145 or the test strip 115 of FIG. 2 is set to the measuring apparatus 131.

The positive terminal 117 and negative terminal 119 are formed in the test strip 141 along the direction orthogonal to the set direction I to be electrically connected to the positive electrode 102 and negative electrode 103 of the measuring apparatus 131. In other words, the test strip 141 does not have a terminal electrically connectable to the type judgement electrode 104 of the measuring apparatus 131.

In contrast, the test strip 145 has a negative terminal 146 and the positive terminal 117. The negative terminal 146 is electrically connected to the type judgement electrode 104 and negative electrode 103 of the measuring apparatus 131 thereby to shortcircuit the type judgement electrode 104 and negative electrode 103. The positive terminal 117 is electrically connected to the positive electrode 102 of the measuring apparatus 131.

When the test strip 141 is set to the measuring apparatus 131, the positive electrode 102 of the measuring apparatus 131 is electrically connected to the positive terminal 117 of the test strip 141, and the negative electrode 103 of the measuring apparatus 131 is electrically connected to the negative terminal 119 of the test strip 141. The type judgement electrode 104 of the measuring apparatus 131 has no electric connection. Therefore, even when the CPU 134 carries out the first through third operations after the test strip 141 is completely set to the apparatus 131, the digital values D5–D7 output from the A/D converter 107 never change. The CPU 134 thus judges based on the absence of a change in the digital values D5–D7 that the test strip 141 with the reaction reagent 142 measurable by the measuring apparatus 131 is set to the measuring apparatus 131. The component is now started to be measured with the measuring apparatus 131.

When the test strip 145 is set to the measuring apparatus 131, the type judgement electrode 104 and negative electrode 103 of the measuring apparatus 131 are electrically connected to the negative terminal 146 of the test strip 145. Consequently the type judgement electrode 104 and negative electrode 103 of the measuring apparatus 131 are shortcircuited, and the positive electrode 102 of the measuring apparatus 131 and positive terminal 117 of the test strip 145 are electrically connected with each other.

After the complete setting of the test strip 145, the CPU 134 executes the above-described first through third operations. Since the type judgement electrode 104 and negative electrode 103 of the concentration measuring apparatus 131 are shortcircuited, and the switch 132 at the input of the amplifier 105 is kept OFF in the first and third operations, the digital values D5, D7 output from the A/D converter 107 do not change. However, the switch 132 is brought into the ON state when the CPU 134 performs the second operation, and the type judgement electrode 104 and negative electrode 103 of the measuring apparatus 131 are shortcircuited and grounded, whereby the input of the amplifier 105 is grounded. As a result, the digital value D6 sent from the A/D converter 107 in the second operation becomes different from the digital values D5, D7.

The CPU 134 judges from the fact that all of the digital values D5–D7 are not equal that the test strip 145 is one not equipped with the reaction reagent 142 measurable by the measuring apparatus 131, not carrying out the component measurement.

When the test strip 115 shown in FIG. 2 is set to the measuring apparatus 131, the type judgement electrode 104 and positive electrode 102 of the measuring apparatus 131 are electrically connected to the positive terminal 117 and type judgement terminal 118 of the test strip 115. In consequence of this, the type judgement electrode 104 and positive electrode 102 of the measuring apparatus 131 are shortcircuited. The negative electrode 103 of the measuring apparatus 131 is electrically connected to the negative terminal 119 of the test strip 115.

After the test strip 115 is completely set, the CPU 134 executes the first through third operations as described earlier. Since the type judgement electrode 104 and positive electrode 102 of the measuring apparatus 131 are shortcircuited, the digital values D5, D6 sent out from the A/D converter 107 do not change in the first and second operations. On the other hand, the switch 133 is turned ON when the CPU 134 executes the third operation, and moreover, since the type judgement electrode 104 and positive electrode 102 of the measuring apparatus 131 are shortcircuited, the input of the amplifier 105 becomes grounded. The digital value D7 from the A/D converter 107 in the third operation is consequently different from the digital values D5, D6.

The CPU 134 judges from the fact that the digital values D5–D7 are not the same that the test strip 115 is one without the reaction reagent 142 measurable by the measuring apparatus 131, and does not start the component measurement.

The circuit constitution of FIG. 4 enables also a measurement of a concentration of the component. In order to measure the concentration, the CPU 134 performs the first operation, turning the switches 132, 133 OFF. For example, blood is dropped onto the reaction reagent 142 of the test strip 141 thereby to measure the concentration of, for instance, lactate in the blood. The operation for the measurement of the concentration is substantially not different from the earlier described operation with respect to the first embodiment, the description of which is accordingly omitted here.

According to the second embodiment as above, only when the test strip 141 with the reaction reagent 142 measurable by the measuring apparatus 131 is set to the measuring apparatus 131, the component to be measured can be measured. Therefore, it is prevented that a test strip designed for measurement of glucose is set inadvertently and a wrong result is obtained although lactate is to be measured.

Since the CPU 134 obtains the digital values D5–D7 as above in the second embodiment, types of the test strips set to the measuring apparatus 131 can be identified if the CPU 134 is adapted to recognize beforehand types of test strips corresponding to the above digital values D5–D7.

Third Embodiment

Figure 7:
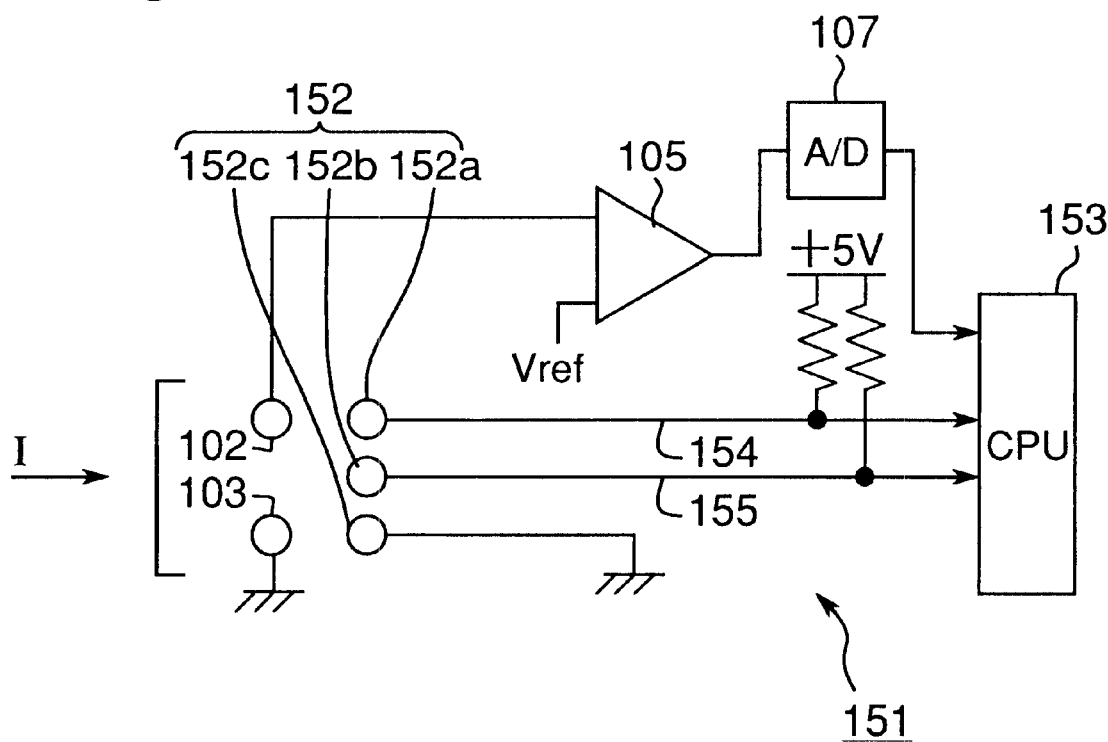
FIG. 7 is a structural diagram of a concentration measuring apparatus according to a third embodiment of the present invention.
Figure 8:
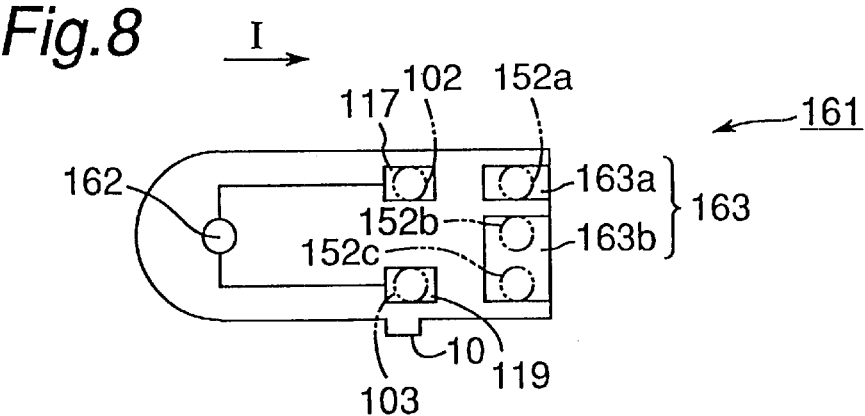
FIG. 8 is a plan view of a test strip to be set to the concentration measuring apparatus and fit to the concentration measuring apparatus of FIG. 7.
Figure 9:
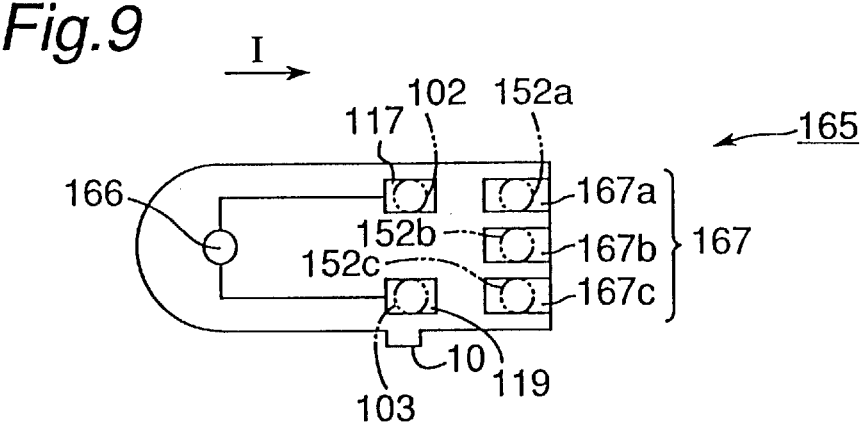
FIG. 9 is a plan view of a test strip to be set to the concentration measuring apparatus and not fit to the concentration measuring apparatus of FIG. 7.

A concentration measuring apparatus and a test strip for the concentration measuring apparatus according to a third embodiment of the present invention are shown in FIGS. 7–9. A CPU 153 described later corresponds to an example of the potential judge device in the "Disclosure Of Invention".

A concentration measuring apparatus 151 in FIG. 7 will be described. The concentration measuring apparatus 151 similarly includes a type judgement electrode 152. As shown in FIG. 7, in the concentration measuring apparatus 151, the positive electrode 102 and negative electrode 103 are arranged in the direction orthogonal to the set direction I at an entrance where a test strip is inserted, and further a first type judgement electrode 152a, a second type judgement electrode 152b and a third type judgement electrode 152c are disposed at an inner side of the measuring apparatus 151 than positions of the positive and negative electrodes 102, 103. The first type judgement electrode 152a, second type judgement electrode 152b, and third type judgement electrode 152c are generically referred to as the type judgement electrode 152.

The positive electrode 102 is connected to the input of the amplifier 105. The output of the amplifier 105 is connected to the CPU 153 via the A/D converter 107. The negative electrode 103 and third type judgement electrode 152c are both grounded. On the other hand, the first type judgement electrode 152a and second type judgement electrode 152b are connected to the CPU 153 via corresponding connecting lines 154, 155 to which a voltage of +5V is normally applied through respective resistors.

Figure 10:
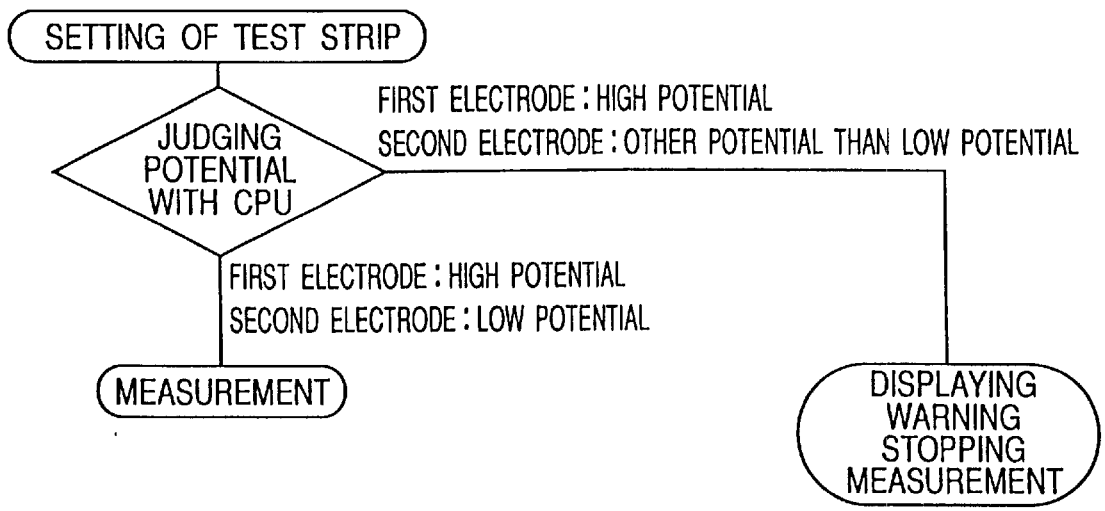
FIG. 10 is a flow chart of operations for identifying the test strip in the concentration measuring apparatus of FIG. 7.

The CPU 153 controls as will be described hereinbelow to measure the concentration of the component in the liquid test sample only when a test strip having a reaction reagent measurable by the measuring apparatus 151 is set to the measuring apparatus 151. More specifically, referring to FIG. 10, when a test strip is set to the measuring apparatus 151, the CPU 153 detects each potential of the first and second type judgement electrodes 152a, 152b obtained via the connecting lines 154, 155. Only in a state of an "appropriate test strip set potential", which is a potential state achieved when a proper test strip is set, that is, the potential of the first type judgement electrode 152a is a high level and that of the second type judgement electrode 152b is a low level, the CPU 153 recognizes that the test strip set in the measuring apparatus 151 is one with the reaction reagent measurable by the apparatus 151, and starts measuring the component in the liquid test sample. If the first and second type judgement electrodes 152a, 152b are not in the above potential state achieved by the proper test strip, the CPU 153 displays, e.g., a warning and refrains from the measurement.

In the embodiment, the CPU 153 is used to judge the potential of the type judgement electrode 152. However, the present invention is not limited to this arrangement and a potential judge device simply for judging of the potential of the type judgement electrode 152 may be provided separately within the measuring apparatus 151.

In addition, a count of the type judgement electrodes is not limited to 3. Four or more type judgement electrodes may be formed to meet a count of types of test strips to be identified, in which case at least one combination of potentials of the type judgement electrodes is adapted to be the above appropriate test strip set potential.

The operation of the thus-constituted concentration measuring apparatus 151 will be discussed. FIGS. 8 and 9 are simplified diagrams of test strips 161, 165 to be set to the concentration measuring apparatus 151. The test strips 161, 165 are fundamentally similar structure to the conventional test strip 1 of FIGS. 33 and 34. Reference numerals 162, 166 of FIGS. 8 and 9 are reaction reagents described earlier. The measuring electrode 5 and counter electrode 6 are hidden by the reaction reagents 162, 166 and not illustrated in the drawings. The test strip 161 is one having the reaction reagent measurable by the measuring apparatus 151 applied thereto, and the component in the liquid test sample cannot be measured by the test strip 165 even when the test strip 165 is set to the measuring apparatus.

The positive terminal 117 and negative terminal 119 are formed in the test strip 161 to be electrically connectable to the positive electrode 102 and negative electrode 103 of the measuring apparatus 151 when the test strip 161 is completely inserted to the measuring apparatus 151. Moreover, a first type judgement terminal 163a is formed in the test strip 161 to be electrically connected with the first type judgement electrode 152a of the measuring apparatus 151. A second type judgement terminal 163b provided in the test strip 161 is electrically connectable to the second and third type judgement electrodes 152b, 152c of the measuring apparatus 151. The first and second type judgement terminals 163a, 163b are referred to altogether as a type judgement terminal 163.

While the test strip 161 is perfectly inserted to the measuring apparatus 151, the second type judgement electrode 152b and third type judgement electrode 152c of the measuring apparatus 151 are shortcircuited by the second type judgement terminal 163b. The potential of the second type judgement electrode 152b becomes the low level because the third type judgement electrode 152c is grounded. Meanwhile, although the first type judgement electrode 152a is connected to the first type judgement terminal 163a of the test strip 161, the first type judgement electrode 152a is maintained at +5V because the first type judgement terminal 163a has no electric connection.

Accordingly, the CPU 153 judges that the first type judgement electrode 152a is the high level and the second type judgement electrode 152b is the low level, namely, the appropriate test strip set potential is satisfied. The CPU 153 recognizes that the test strip inserted to the measuring apparatus 151 is one equipped with the reaction reagent measurable by the measuring apparatus 151, thereby starting the measurement of the component in the liquid test sample.

The test strip 165 has the positive terminal 117 and negative terminal 119, similar to the test strip 161. The test strip 165 also has a first type judgement terminal 167a, a second type judgement terminal 167b and a third type judgement terminal 167c which are electrically connectable to the first type judgement electrode 152a, second type judgement electrode 152b and third type judgement electrode 152c of the measuring apparatus 151 respectively when the test strip 165 is completely set to the measuring apparatus 151. These first, second, and third type judgement terminals 167a, 167b, 167c are independent of one another without any mutual electric connection.

While the test strip 165 in the above constitution is completely inserted to the measuring apparatus 151, because of the absence of the mutual electric connection among the first, second, and third type judgement terminals 167a, 167b and 167c of the test strip 165, the first type judgement electrode 152a and second type judgement electrode 152b of the measuring apparatus 151 are maintained in the state with the +5V applied thereto. Therefore, the CPU 153 judges that the first and second type judgement electrodes 152a, 152b are both the high level, thereby recognizing that the test strip 165 set to the measuring apparatus 151 is not the one with the reaction reagent measurable by the measuring apparatus 151. The measurement of the component is not conducted in the CPU 153.

The concentration of the component can also be measured in the circuit constitution in FIG. 7. For example, blood is dropped to the reaction reagent 162 of the test strip 161, and the concentration of, e.g., glucose in the blood is measured via the positive and negative electrodes 102 and 103 of the measuring apparatus 151. Since the measurement operation is not different fundamentally from in the first embodiment, the description thereof will be omitted.

According to the third embodiment, only when the test strip 161 with the reaction reagent 162 measurable by the measuring apparatus 151 is set to the measuring apparatus 151, the component measurement is allowed. Such an inadvertent accident is thus prevented that a test strip for measurement of lactate is set inadvertently to the measuring apparatus 151 and a wrong result is obtained although glucose is required to be measured.

In the above embodiment, although at least two type judgement terminals (163a and 163b) are formed in the test strip, a count of the terminals is not restricted to this. In the event that four or more type judgement electrodes are provided in the measuring apparatus, at least two type judgement terminals are to be formed, so that the potential judge device can judge the appropriate test strip set potential from a combination of connections of the type judgement electrodes and type judgement terminals.

Fourth Embodiment

A concentration measuring apparatus and a test strip for the concentration measuring apparatus according to a fourth embodiment of the present invention are indicated in FIGS. 11 through 15. A CPU 173 to be described later functions as an example of the change judge device described in the "Disclosure Of Invention".

Figure 11:
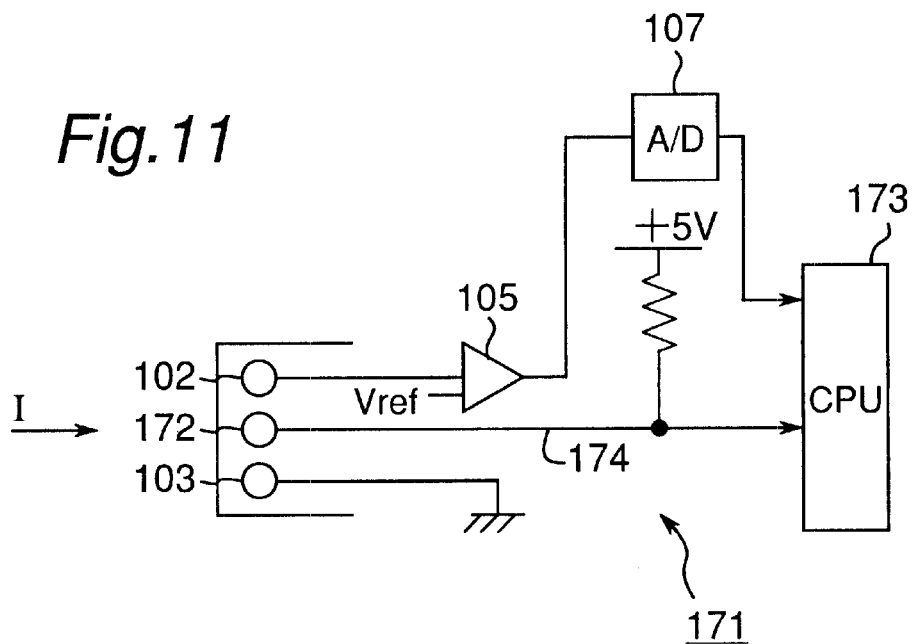
FIG. 11 is a structural diagram of a concentration measuring apparatus according to a fourth embodiment of the present invention.

A concentration measuring apparatus 171 of FIG. 11 will be depicted below. The concentration measuring apparatus 171 is similarly provided with a type judgement electrode 172. As is shown in FIG. 11, the positive electrode 102, type judgement electrode 172, and negative electrode 103 are arranged in the direction orthogonal to the set direction I. The positive electrode 102 is connected to the input of the amplifier 105 having the output thereof connected to the CPU 173 via the A/D converter 107. The negative electrode 103 is grounded. The type judgement electrode 172 is connected to the CPU 173 via a connecting line 174. A voltage of +5V is normally applied to the connecting line 174 via a resistor.

Figure 14:
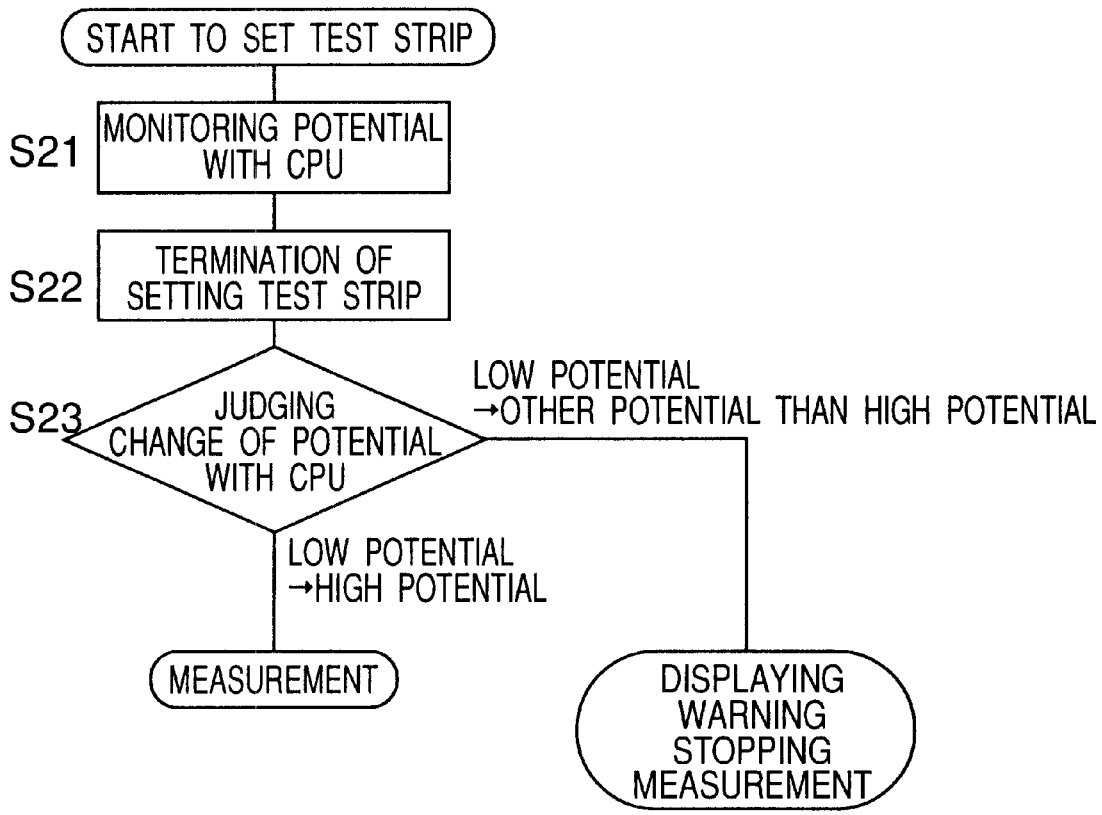
FIG. 14 is a flow chart of operations for identifying the test strip in the concentration measuring apparatus of FIG. 11.
Figure 15:
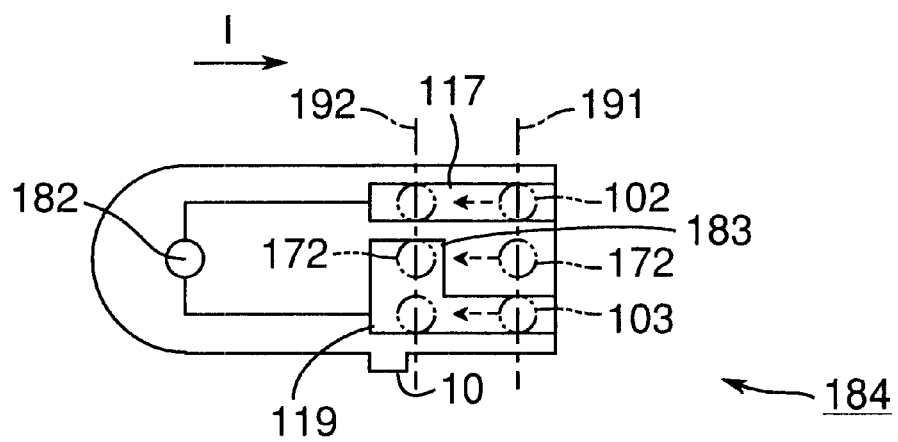
FIG. 15 is a plan view of a test strip of a different embodiment to be set to the concentration measuring apparatus of FIG. 11.

The CPU 173 controls in the following fashion to measure the concentration of the component in the liquid test sample only when a test strip with a reaction reagent measurable by the measuring apparatus 171 is set to the measuring apparatus 171. Referring to FIG. 14, the CPU 173 detects potentials of the type judgement electrode 172 immediately after a test strip is inserted to the measuring apparatus 171 in step (designated by S in FIG. 14) 21 and when the test strip is completely set to the apparatus 171 in step 22. A change of potentials between the two time points is detected in step 23. More specifically, the CPU 173 judges whether or not the change of the potentials corresponds to an "appropriate test strip set change" which is to be brought about only when an appropriate test strip with the reaction reagent measurable by the measuring apparatus 171 is set to the measuring apparatus 171. When the potential change is the appropriate test strip set change, the CPU 173 recognizes that the test strip with the reaction reagent measurable by the measuring apparatus 171 is set to the measuring apparatus 171, thereby to start the component measurement. When judging that the potential change is not the appropriate test strip set change, the CPU 173 makes, for instance, a warning display, etc, not starting the measurement.

In the above embodiment, the CPU 173 detects potentials of the type judgement electrode 172 at the above both time points thereby to judge the potential change. However, the present invention is not restricted to the embodiment, and a change judge device for detecting the potentials and judging the potential change may be installed separately in the measuring apparatus 171.

The operation of the concentration measuring apparatus 171 will be depicted. Test elements 181, 185 in FIGS. 12 and 13 to be set to the measuring apparatus 171 and illustrated in a simplified manner are fundamentally similar structure to the conventional test strip 1 of FIGS. 33 and 34. Reference numerals 182, 186 in FIGS. 12 and 13 correspond to the reaction reagent. The measuring electrode 5 and counter electrode 6 arranged are hidden by the reaction reagents 182, 186 and not seen in the drawings. The test strip 181 has the reaction reagent measurable by the measuring apparatus 171 applied thereto, and the test strip 185 cannot measure the component in the liquid test sample even when set to the measuring apparatus 171.

Corresponding to the positive electrode 102 and negative electrode 103 of the concentration measuring apparatus 171, the positive terminal 117 and negative terminal 119 are extended along the set direction I in the test strip 181. Moreover, a type judgement terminal 183 is formed in the test strip 181 which is electrically connected to the type judgement electrode 172 of the concentration measuring apparatus 171 only immediately after the test strip 181 is inserted to the measuring apparatus 171 in the set direction I. The type judgement terminal 183 is integrally formed with the negative terminal 119.

Figure 12:
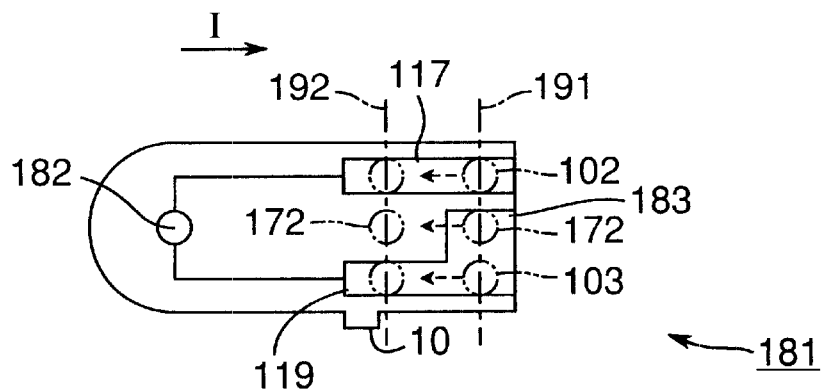
FIG. 12 is a plan view of a test strip to be set to the concentration measuring apparatus and fit to the concentration measuring apparatus of FIG. 11.

As is clear from FIG. 12, immediately after the insertion of the test strip 181 to the measuring apparatus 171 along the set direction I, the positive electrode 102, type judgement electrode 172, and negative electrode 103 of the measuring apparatus 171 are located on a line designated by a reference numeral 191, and electrically connected respectively to the positive terminal 117, type judgement terminal 183 and negative terminal 119. Since the type judgement terminal 183 and negative terminal 119 of the test strip 181 are integrated, the type judgement electrode 172 and negative electrode 103 of the measuring apparatus 171 are shortcircuited immediately after the insertion. Since the negative electrode 103 is grounded, the potential of the type judgement electrode 172 of the measuring apparatus 171 becomes a grounding level, namely, low level.

When the test strip 181 is further inserted in the set direction I and fully set to the measuring apparatus 171, the positive electrode 102, type judgement electrode 172, and negative electrode 103 of the measuring apparatus 171 are present on a line 192. In this state, the positive electrode 102 and negative electrode 103 are maintained in a state electrically connected to the positive terminal 117 and negative terminal 119. However, the type judgement electrode 172 of the measuring apparatus 171 is not electrically connected because of absence of a terminal at a position corresponding to the type judgement electrode 172 on the test strip 181. When the test strip is completely set, the potential of the type judgement electrode 172 of the measuring apparatus 171 is changed to +5V, i.e., high level.

As described hereinabove, when the test strip 181 with the reaction reagent 182 measurable by the measuring apparatus 171 is set to the measuring apparatus 171, the potential of the type judgement electrode 172 of the measuring apparatus 171 changes from the initial high level to the low level consequent to the insertion of the test strip 181, and returns to the high level again when the insertion is completed, that is, the earlier-mentioned appropriate test strip set change is brought about. The CPU 173 detects the appropriate test strip set change, thereby recognizing that the test strip 181 with the reaction reagent 182 measurable by the measuring apparatus 171 is set to the measuring apparatus 171, and starting the measurement of the component in the liquid test sample.

Figure 13:
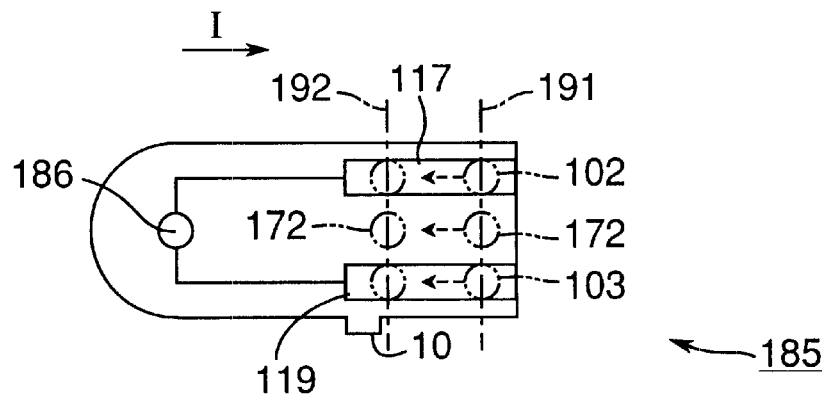
FIG. 13 is a plan view of a test strip to be set to the concentration measuring apparatus and not fit to the concentration measuring apparatus of FIG. 11.

Incidentally, only the positive terminal 117 and negative terminal 119 are formed in the test strip 185, without the type judgement terminal 183. Therefore, immediately after the test strip 185 is inserted to the measuring apparatus 171 along the set direction I, as shown in FIG. 13, the positive electrode 102, type judgement electrode 172, and negative electrode 103 of the measuring apparatus 171 are located on the line 191, so that the positive electrode 102 and negative electrode 103 are electrically connected to the positive terminal 117 and negative terminal 119 respectively. The type judgement electrode 172 has no electric connection because the test strip 185 is not provided with a terminal corresponding to the type judgement electrode 172. The type judgement electrode 172 is accordingly maintained at +5V immediately after the insertion.

When the test strip 185 is further inserted along the set direction I and completely set to the measuring apparatus 171, the positive electrode 102, type judgement electrode 172, and negative electrode 103 are on the line 192, with the positive electrode 102 and negative electrode 103 being kept in the electrically connected state with the positive terminal 117 and negative terminal 119 respectively. Since a terminal corresponding to the type judgement electrode 172 is not formed in the test strip 185, the type judgement electrode 172 of the measuring apparatus 171 has no electric connection, and is held at +5V, namely, high level even at the completion of the insertion.

The potential of the type judgement electrode 172 of the measuring apparatus 171 does not change from the original high level when the test strip 185 with the reaction reagent 186 which cannot be measured by the measuring apparatus 171 is set to the measuring apparatus 171. Therefore, the CPU 173 recognizes that the test strip 185 having the reaction reagent 186 is set to the measuring apparatus 171 and does not start the measurement of the component in the liquid test sample.

According to the fourth embodiment, the appropriate test strip set change at the type judgement electrode 172 of the measuring apparatus 171 is adapted to represent the high level initially, low level subsequent to the insertion of the test strip and high level again when the insertion is completed. The potential change is not limited to this pattern and is determined by a shape of the type judgement terminal formed in the test strip correspondingly to the type judgement electrode 172. For example, a test strip 184 in FIG. 15 may be designed to assume the potential change, i.e. the appropriate test strip set change from the high level when the test strip is inserted to the low level when the insertion is complete.

The concentration of the component is measured in the circuit constitution of FIG. 11. For instance, blood is dropped to the reaction reagent 182 of the test strip 181 and, a concentration of glucose in the blood is measured via the positive electrode 102 and negative electrode 103 of the measuring apparatus 171. The operation for measuring the concentration as above is not basically different from the description of the first embodiment, the description of which is accordingly omitted.

According to the fourth embodiment, only when the test strip 181 having the reaction reagent 182 measurable by the measuring apparatus 171 is set to the measuring apparatus 171, the component can be measured. Such an inconvenience is prevented that a test strip for measurement of lactate is set inadvertently to the measuring apparatus 171 and a wrong result is obtained although glucose is required to be measured.

In the foregoing embodiments, while each concentration measuring apparatus is adapted to identify the test strip conforming to each concentration measuring apparatus, the test strips cannot be used in common among the measuring apparatuses. For example, the test strip 115 of FIG. 2 is appropriate to the measuring apparatus 101 of FIG. 1, similarly, the test strip 141 of FIG. 5 to the measuring apparatus 131 of FIG. 4. Even when the test strip 141 of FIG. 5 is set to the measuring apparatus 101, the component measurement cannot be executed in the measuring apparatus 101. Similarly, even though the test strip 115 of FIG. 1 is set to the measuring apparatus 131, the measuring apparatus 131 cannot execute the component measurement. From this, the present invention in the embodiments can realize a biosensor system which prohibits test strips from being shared among different concentration measuring apparatuses.

Figure 16:
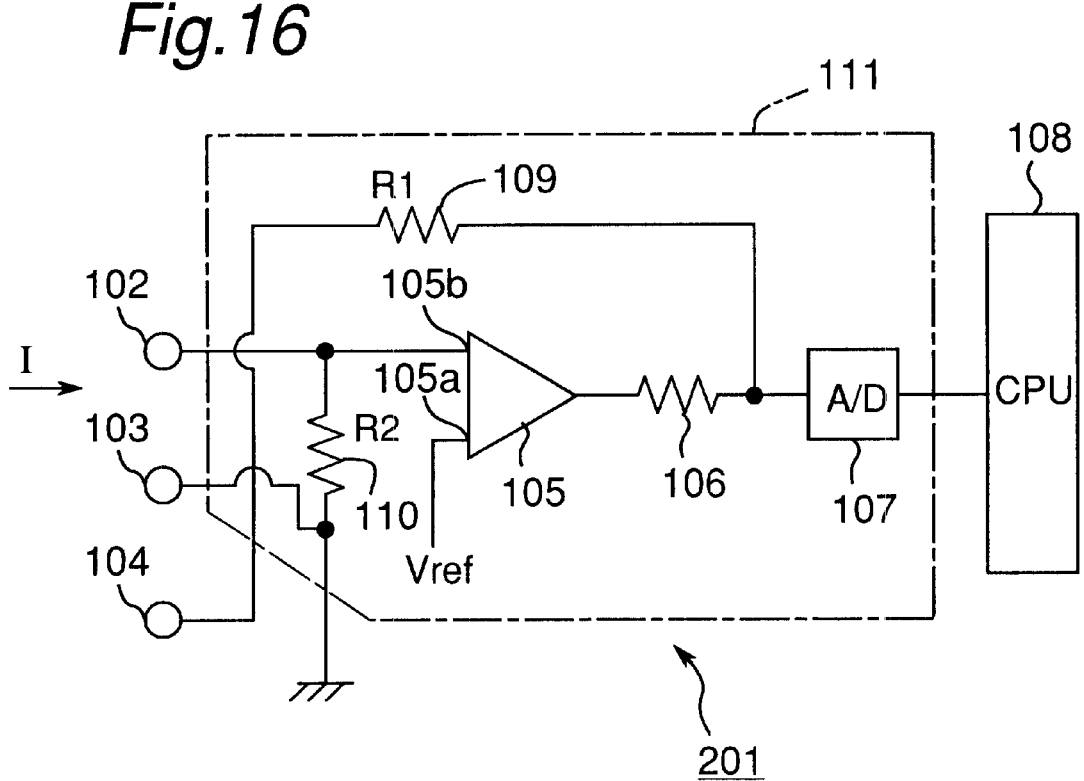
FIG. 16 is a diagram of a modified example of the concentration measuring apparatus of FIG. 1.
Figure 17:
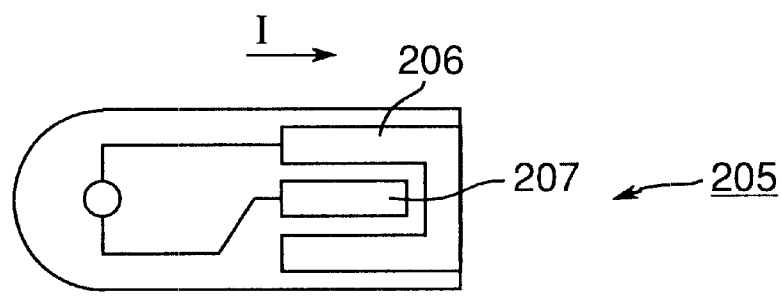
FIG. 17 is a plan view of a test strip fit to the concentration measuring apparatus of FIG. 16.

FIG. 16 is a modified example of the concentration measuring apparatus 101 of FIG. 1. A concentration measuring apparatus 201 may be constituted of the positive electrode 102, negative electrode 103, and type judgement electrode 104 arranged in this order in the direction orthogonal to the set direction I. A test strip 205 capable of measuring the component in the measuring apparatus 201 is shown in FIG. 17. The test strip 205 has a first terminal 206 for electrically connecting the positive electrode 102 and type judgement electrode 104 of the measuring apparatus 201. Moreover, a second terminal 207 is formed which is electrically connected to the negative electrode 103 of the measuring apparatus 201.

Even when the test strip 115 conforming to the measuring apparatus 101 is set to the measuring apparatus 201, the component measurement is impossible. Also, even when the test strip 205 matching the measuring apparatus 201 is set to the measuring apparatus 101, the component cannot be measured. That is because the positive electrode 102 and type judgement electrode 104 are not shortcircuited in any case. As above, the present invention can provide by changing constitutions the biosensor system wherein the test strips cannot be shared even among the measuring apparatuses of the same embodiment.

Basically the concentration measuring apparatus in each embodiment described hereinabove is capable of measuring one kind of component, e.g., glucose, and is adapted to execute the measurement of the concentration of glucose only when the test strip with the reaction reagent fit for the measurement of glucose is set thereto. However, the above concentration measuring apparatuses in each embodiment and a concentration measuring apparatus according to a fifth embodiment to be described below are not limited to this model. For example, the measuring apparatus is devisable and may be set when shipped or before used so that it can measure a plurality of required kinds of components, and the concentration measurement is executed only when the corresponding test strips to the required components are inserted.

In the foregoing description, the type judgement electrode and type judgement terminal are used to detect whether or not the test strip corresponding to the component to be measured by the measuring apparatus is set to the measuring apparatus. However, the technical idea of using the type judgement electrode and type judgement terminal is not limited to the idea of the above-mentioned embodiments, which is utilizable, for example, to calibrate the measuring apparatus as in the following fifth embodiment. The calibration executed in the measuring apparatus includes at least compensation for an error in component concentration through the selection of a required calibration curve among a plurality of calibration curves, and checking of the operation of the measuring apparatus based on whether or not a predetermined concentration value is displayed when the test strip adjusted beforehand to display the predetermined concentration value is set to the measuring apparatus. The fifth embodiment exemplifies the above selection of the calibration curve.

Fifth Embodiment

As described in the beginning of the "Best Mode for Carrying Out the Invention", the enzyme included in the reaction reagent applied on the base material of the test strip correspondingly to the component to be measured has a production error for each production lot. For instance, when a liquid test sample containing glucose of a concentration of 100 mg/dl is dropped to a glucose reaction reagent including an enzyme of a first production lot, a measuring apparatus displays 100 mg/dl. On the other hand, when the same liquid test sample is dropped to a reaction reagent including an enzyme of a second production lot, the measuring apparatus displays 90 mg/dl. An error is included in the measured values as above due to the production error of the enzyme itself. Although a factor causing the largest error in the measured values is the production error of the enzyme, resistance values at the positive terminal, negative terminal, etc. formed on the base material of the test strip induce the error as well, because the conductive carbon paste which is printed to form the terminals is also not free from the production error.

For eliminating the above problem, conventionally, calibration curve information for compensating for an estimated error in measured concentration thereby displaying a true concentration is stored beforehand in the measuring apparatus as disclosed, e.g., in the Japanese Patent Laid-Open Publication No. 4-357452. And, a calibration test strip for selecting calibration curve information that can compensate for the production error of each production lot from a plurality of calibration curve information is prepared for every group of test strips having the same production lot. Since the large influential factor for the measurement error is the production error of the enzyme, the same production lot generally corresponds to a group of test strips to which the reaction reagent including the enzyme of the same production error is applied. Conventionally, a user when using the test strip of a different production lot should first set the calibration test strip to the measuring apparatus and then select the calibration curve information corresponding to the production lot of the test strip used. So long as test strips used are of the same production lot, it is enough to select the calibration curve information once, and not necessary to select the information every time each test strip of the same production lot is used.

As described hereinabove, in the conventional concentration measuring apparatus, the user is required to pay attention to a change of the enzymes of the test strips, namely, a change of the production lots. Unless the calibration curve information corresponding to the production error of the enzyme is selected, a large error is included in the measured values displayed at the measuring apparatus.

The fifth embodiment is devised to solve the problem, in which a function of selecting the calibration curve information is exerted by the type judgement electrode, type judgement terminal, and CPU on the basis of the technical concept of the use of the type judgement electrode and type judgement terminal described in the foregoing embodiments.

As will be described hereinbelow, the fifth embodiment is constituted to be a modification of the fourth embodiment, because as every one component to be measured generally has ten or more kinds of calibration curve information, it is necessary that type judgement terminals of the test strip distinguish the ten or more kinds of calibration curve information with as a small count of the type judgement terminals as possible. However, the selection of the calibration curve information is enabled not only by the modified constitution of the fourth embodiment, but a modification of the above second or third embodiment can handle the selection in some cases if the calibration curve information to be distinguished comprises only several kinds or so.

The fifth embodiment is so constituted as to select the calibration curve information by the type judgement terminal formed in the test strip, the type judgement electrode and CPU of the measuring apparatus, and at the same time, judge the measurable component, similar to the first through fourth embodiments. The fifth embodiment is not restricted to this constitution and, may be adapted simply to select the calibration curve information.

A concentration measuring apparatus and a test strip for the concentration measuring apparatus according to the fifth embodiment will be explained with reference to FIGS. 19 through 24. CPUs 258, 308 and 358 to be described hereinbelow are embodiments to exert a function of the "change judge device".

Figure 19:
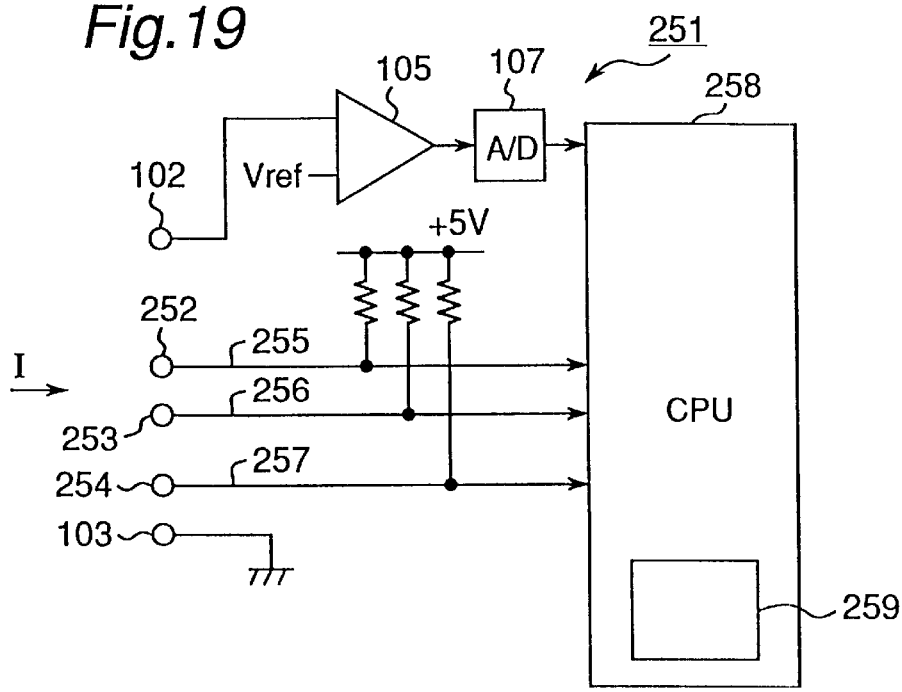
FIG. 19 is a structural diagram of a concentration measuring apparatus according to a fifth embodiment of the present invention.
Figure 20:
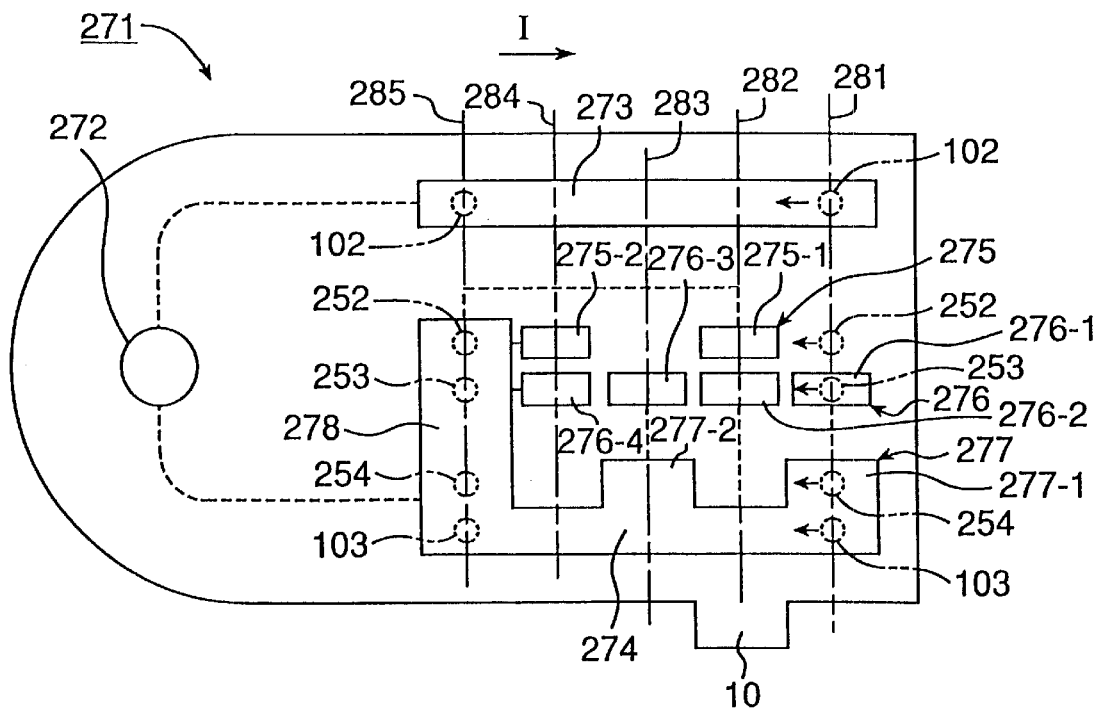
FIG. 20 is a plan view of a test strip to be set to the concentration measuring apparatus of FIG. 19.
Figure 21:
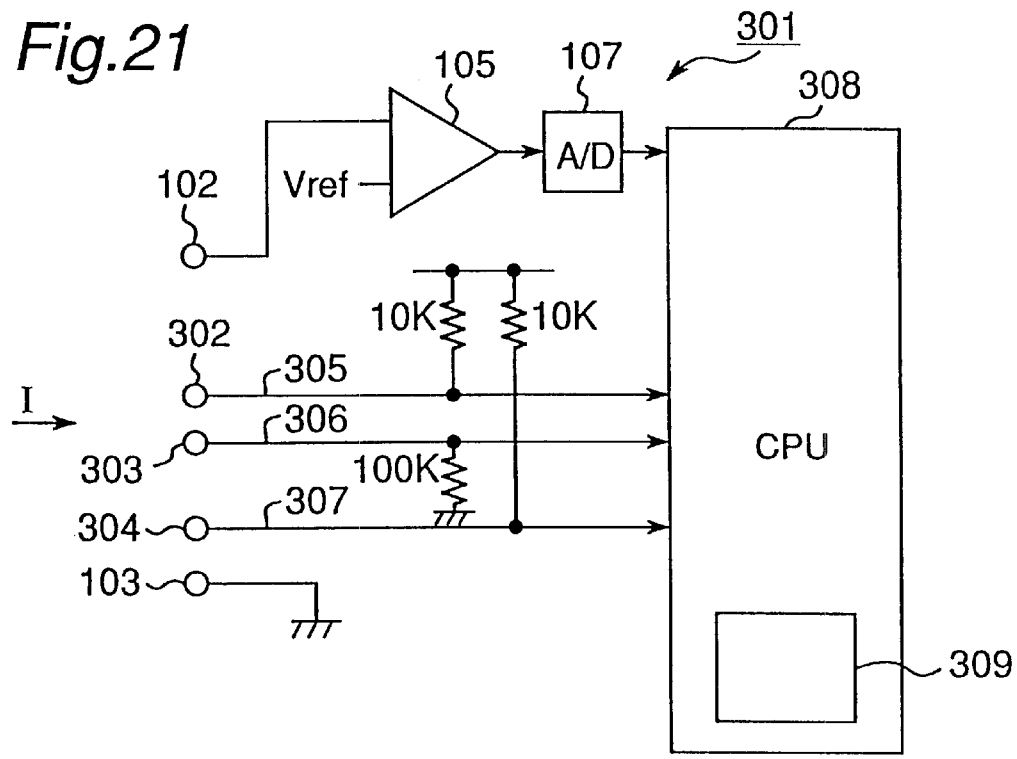
FIG. 21 is a structural diagram of a modification of the concentration measuring apparatus of FIG. 19.
Figure 22:
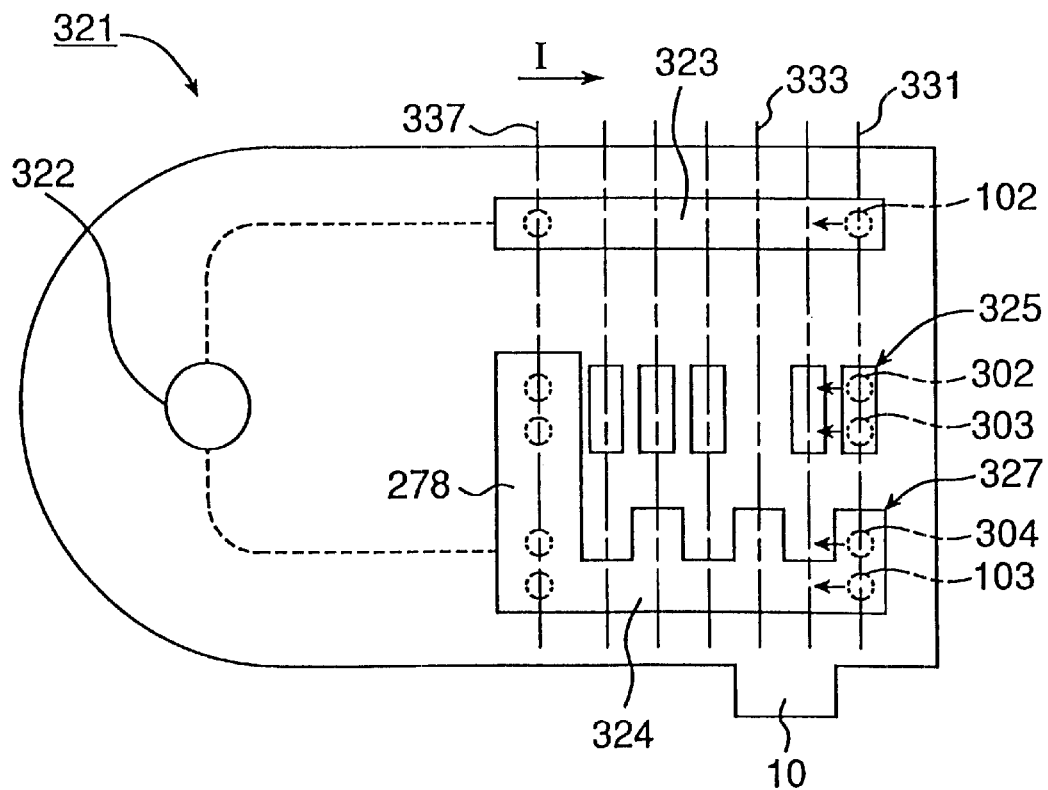
FIG. 22 is a plan view of a test strip to be set to the concentration measuring apparatus of FIG. 21.

FIG. 19 indicates a concentration measuring apparatus 251 of an example of the fifth embodiment, and FIG. 20 is a test strip 271 to be set to the concentration measuring apparatus 251.

The concentration measuring apparatus 251 corresponds to a modification of the concentration measuring apparatus 171 of the fourth embodiment described with reference to FIG. 11, having the positive electrode 102, three type judgement electrodes 252, 253 and 254, and negative electrode 103 arranged in the direction orthogonal to the set direction I of the test strip 271. The positive electrode 102 is connected to the input of the amplifier 105 which has the output connected to the CPU 258 via the A/D converter 107. The negative electrode 103 is grounded. The type judgement electrodes 252–254 are connected to the CPU 258 via respective connecting lines 255–257. Generally, each voltage of +5V is applied via resistors to each of the connecting lines 255–257.

The CPU 258 is provided with a memory part 259 storing a plurality of calibration curve information for the compensation of the measurement error in concentration of the specific component included in the liquid test sample. Similar to the measuring apparatus of each embodiment described above, the CPU 258 carries out control to measure the concentration only when the test strip 271 with the reaction reagent measurable by the concentration measuring apparatus 251 is set to the measuring apparatus 251, and select and extract from the memory part 259 in accordance with the production lot of the test strip 271 set in the measuring apparatus 251 a predetermined calibration curve information that can compensate for the measurement error. Although an operation of the CPU 258 will be discussed in detail later, basically, the CPU 258 detects potential change patterns generated at each of the type judgement electrodes 252, 253 and 254 after the test strip 271 is started to be inserted in the set direction I to the measuring apparatus 251 before the test strip 271 is completely set to the apparatus 251, that is, the appropriate test strip set change as described in the fourth embodiment and also detects a "calibration curve information selection change" to be described later. Based on the detected appropriate test strip set change, the CPU 258 judges whether or not the test strip having the reaction reagent to react with the specific component measurable by the measuring apparatus 251 is set to the apparatus 251. Moreover, based on the detected calibration curve information selection change, the CPU 258 selects a calibration curve information by which the error in the measured concentration by the set test strip can be calibrated.

The type judgement electrodes 252–254 can be divided to a first electrode and a second electrode. The first electrode generates the appropriate test strip set change from the high level to the low level and from the low level to the high level after the test strip is started to be inserted before the test strip is perfectly set in the measuring apparatus, and generates the calibration curve information selection change. In the fifth embodiment, the type judgement electrodes 252 and 253 work as the first electrode. The low level potential corresponds to the grounding level in the embodiment and, the high level potential corresponds to +5V. The second electrode alternately generates the high and low level potentials in synchronization with the potential change at the first electrode so as to detect timings of the appropriate test strip set change and the calibration curve information selection change of the first electrode. The type judgement electrode 254 corresponds to the second electrode in the fifth embodiment.

Although the first electrode is comprised of two electrodes in the fifth embodiment, a count of electrodes of the first electrode is not specifically restricted to this.

Figure 33:
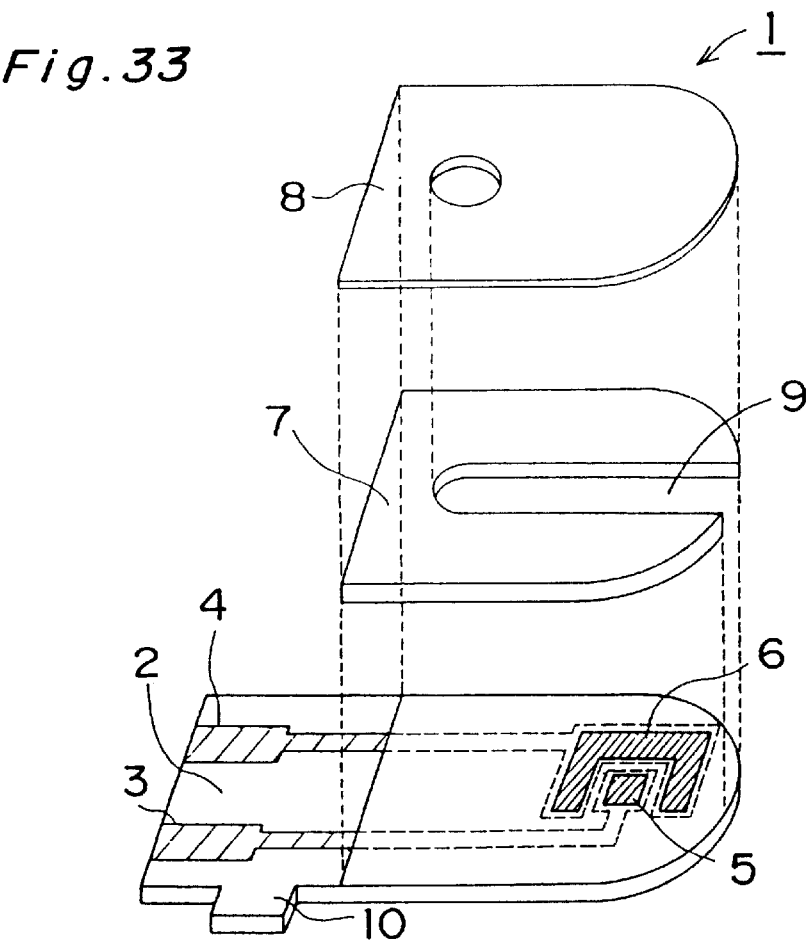
FIG. 33 is an exploded perspective view showing a structure of a conventional test strip.
Figure 34:
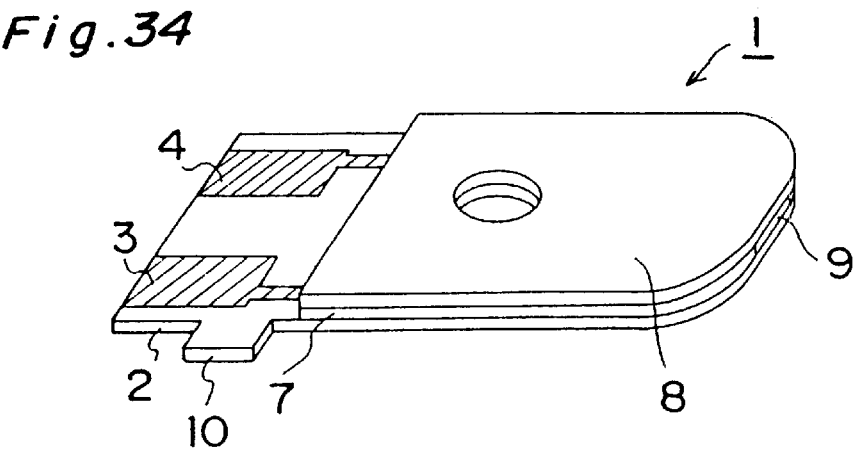
FIG. 34 is a perspective view of a state when the test strip of FIG. 33 is assembled.
Figure 35:
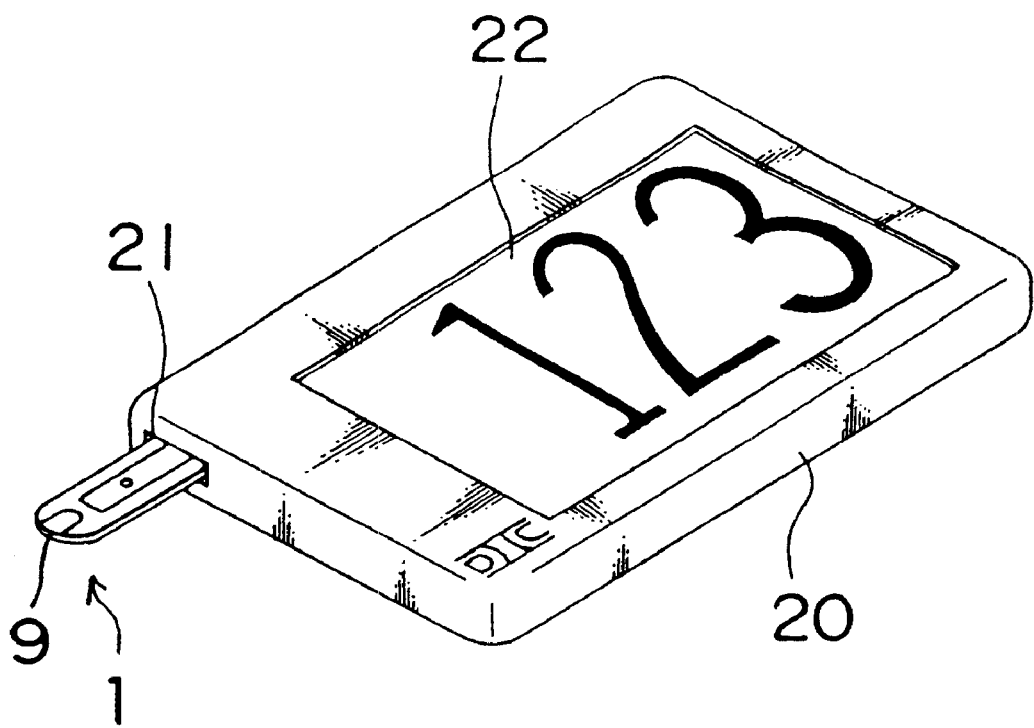
FIG. 35 is a perspective view of a state when the conventional test strip is set to a conventional concentration measuring apparatus.

The test strip 271 of FIG. 20 is fundamentally formed similar structure to the conventional test strip 1 shown in FIGS. 33 and 34. A reference numeral 272 corresponds to the reaction reagent, which hides the measuring electrode 5 and counter electrode 6 in the drawing. The reaction reagent measurable by the measuring apparatus 251 is applied to the test strip 271.

The test strip 271 has a positive terminal 273 and a negative terminal 274 extended in the set direction I to be electrically connected to the positive electrode 102 and negative electrode 103 of the measuring apparatus 251 respectively. The electric connection between the positive electrode 102 and positive terminal 273 and between the negative electrode 103 and negative terminal 274 is maintained while the test strip 271 moves in the I direction after started to be inserted to the measuring apparatus 251 before completely set to the measuring apparatus 251. The test strip 271 is further equipped with type judgement terminals 275, 276 and 277 corresponding to the type judgement electrodes 252, 253 and 254 of the measuring apparatus 251. Two type judgement terminals 275-1 and 275-2 constituting the type judgement terminal 275 are formed discontinuously on a passage of the type judgement electrode 252, and moreover four type judgement terminals 276-1 through 276-4 constituting the type judgement terminal 276 are formed discontinuously on a passage of the type judgement electrode 253 so as to bring about the appropriate test strip set change and the calibration curve information selection change to the type judgement electrodes 252 and 253 during the movement of the test strip 271 along the direction I after started to be inserted to the measuring apparatus 251 before finally set to the measuring apparatus 251. The type judgement terminals 275 and 276 correspond to a part for generating potential change to the first electrode. The type judgement terminals 275-1 and 275-2, and type judgement terminals 276-1 through 276-4 are connected to the negative terminal 274 via connecting lines. The connecting lines are electrically insulated from the type judgement electrodes 252–254 so as to prevent the electric connection between the type judgement electrodes 252–254 and the connecting lines consequent to the movement of the type judgement electrodes 252–254.

In order to generate timings for the appropriate test strip set change and the calibration curve information selection change to the type judgement electrode 254 during the movement of the test strip 271 in the set direction I after started to be inserted to the measuring apparatus 251 before completely set to the measuring apparatus, two type judgement terminals 277-1 and 277-2 constituting the type judgement terminal 277 are formed discontinuously on a passage of the type judgement electrode 254. The type judgement terminal 277 corresponds to a part for generating timings for the second electrode. In the embodiment, the type judgement terminals 277-1 and 277-2 are formed integrally with the negative terminal 274.

Meanwhile, a set completion detection terminal 278 is formed integrally with the negative terminal 274 in the test strip 271 so that the measuring apparatus 251 detects when the test strip 271 is completely set to the apparatus 251.

The above-described positive terminal 273, negative terminal 274, type judgement terminals 275–277 and set completion detection terminal 278 are formed by printing of a conductive material or the like, similar to the prior art. A formation method of the terminals will be described more in detail later.

Although six type judgement terminals 275 and 276 are provided as the part for the potential change to the first electrode according to the fifth embodiment, a count of the type judgement terminals is not confined to this and can be determined by a count of kinds of calibration curve information to be selected and so on.

The concentration measuring apparatus 251 constituted as above operates in the following fashion.

In FIG. 20, at a time point immediately after the test strip 271 is inserted to the measuring apparatus 251 in the set direction I, the positive electrode 102, type judgement electrodes 252–254, and negative electrode 103 of the measuring apparatus 251 are placed at a position shown by a line 281. The positive electrode 102 is electrically connected to the positive terminal 273 of the test strip 271, the type judgement electrodes 253 and 254 are respectively electrically connected to the type judgement terminals 276-1 and 277-1, and the negative electrode 103 is electrically connected to the negative terminal 274, whereas the type judgement electrode 252 without a corresponding terminal thereto has no electric connection. The type judgement terminals 275-1, 275-2 and 276-1 through 276-4 are electrically connected to the negative terminal 274, and the type judgement terminals 277-1 and 277-2 are integrally formed with the negative terminal 274. As a result, the grounded negative electrode 103 is electrically connected to the negative terminal 274, then the type judgement terminals 275-1, 275-2, 276-1 through 276-4 and 277-1, 277-2 are turned to the low level potential, that is, grounding potential in the embodiment via the negative terminal 274. At the time point 281 when the test strip is started to be inserted, the type judgement electrodes 253, 254 and negative electrode 103 are the grounding potential, namely, the low level potential, and the connecting lines 256, 257 connected to the type judgement electrodes 253, 254 are the grounding potential, while the connecting line 255 connected to the type judgement electrode 252 is +5V, i.e., the high level potential.

In accordance with the further insertion of the test strip 271 to the measuring apparatus 251 along the set direction I, when the positive electrode 102, type judgement electrodes 252, 253, 254, and negative electrode 103 are present at a position shown by a line 282, the positive electrode 102 keeps the connection to the positive terminal 273, the negative electrode 103 also maintains the connection to the negative terminal 274 and the type judgement electrodes 252, 253 are connected electrically to the type judgement terminals 275-1, 275-2 respectively. While, the type judgement electrode 254 has no corresponding terminal thereto, and therefore is not electrically connected. At the position 282, therefore, the type judgement electrodes 252 and 253, and negative electrode 103 are the grounding potential, the connecting line 255 connected to the type judgement electrode 252 and connecting line 256 are the grounding potential and, the connecting line 257 connected to the type judgement electrode 254 is +5V, namely, the high level potential.

Similarly, when the test strip 271 is advanced in the set direction I to the measuring apparatus 251 and then the positive electrode 102, type judgement electrodes 252–254 and negative electrode 103 are present at a position shown by a line 283, the positive electrode 102 holds the connected state to the positive terminal 273 and the negative electrode 103 likewise holds the connection to the negative terminal 274, with the connecting line 255 brought to the high level potential and the connecting lines 256 and 257 changed to the grounding potential. Thereafter, when the test strip 271 is inserted in the set direction I to the measuring apparatus 251 thereby to locate the positive electrode 102, type judgement electrodes 252–254 and negative electrode 103 at a position shown by a line 284, the positive electrode 102 is maintained in the connected state to the positive terminal 273, the negative electrode 103 is still connected to the negative terminal 274, the connecting lines 255 and 256 become the grounding potential and the connecting line 257 is changed to the high level potential. With the positive electrode 102, type judgement electrodes 252–254 and negative electrode 103 present at a position shown by a line 285 when the test strip 271 is finally set to the measuring apparatus 251, each connected state of the positive electrode 102 to the positive terminal 273 and of the negative electrode 103 to the negative terminal 274 is retained, and the connecting lines 255–257 are all turned to the grounding potential.

In accordance with the movement of the test strip 271 after the test strip 271 is started to be set before the test strip 271 is completely set to the measuring apparatus 251, in other words, in accordance with the movement of the positive electrode 102, type judgement electrodes 252–254, and negative electrode 103 from the position 281 to the position 285, the CPU 258 of the measuring apparatus 251 detects the potential change at the type judgement electrodes 252–254, namely, connecting lines 255–257. More specifically, when the test strip 271 is completely set to the measuring apparatus 251 and when the CPU 258 detects that every connecting line 255–257 reaches the grounding potential, the CPU 258 judges that the test strip 271 is inserted to a set completion position of the measuring apparatus 251. The connecting line 257 changes from the grounding potential→high level potential→grounding potential→high level potential to the grounding potential in accordance with the movement of the test strip 271 from a start position to the completion position. In other words, the grounding potential and high level potential are alternately repeated at the connecting line 257. The CPU 258 detects the alternating potential change at the connecting line 257. Based on the alternating potential change, the CPU 258 obtains a detection timing of the appropriate test strip set change which is the potential change at the connecting lines 255, 256 and also checks whether or not the test strip 271 is normally set to the measuring apparatus 251. That is, only when the connecting line 257 becomes the high level potential twice after the start position to the set completion position of the test strip 271, the CPU 258 judges that the test strip 271 is set normally to the measuring apparatus 251. In other cases than the above, the CPU 258 judges that the test strip 271 moves in an opposite direction to the set direction I at least once, in other words, the test strip 271 returns, and shows, for example, an error display.

Synchronously with the potential change of the connecting line 257, the CPU 258 detects the appropriate test strip set change which is developed at the connecting lines 255, 256. Specifically, in the fifth embodiment, when the test strip 271 is normally set to the measuring apparatus 251 from the start to the completion of the setting, the connecting line 255 changes from the high level potential→grounding potential→high level potential→grounding potential to the grounding potential, and the connecting line 256 changes from the grounding potentials→grounding potential→grounding potential→grounding potential to the grounding potential. The CPU 258 recognizes a pattern of the potential change at each of the connecting lines 255 and 256 while the type judgement electrodes 252, 253 are moved to locate from the positions 281 through 284. In the present embodiment, since there are six type judgement terminals 275, 276 at positions 281 through 284, the potential change can be $2^6$, namely 64 patterns at maximum. These 64 patterns of the potential change correspond to the calibration curve information and further in the embodiment, information of the specific component measurable by the set test strip 271, stored in the memory part 259. In the fifth embodiment, the CPU 258 selects the information of the specific component, namely, information for the identification of the type of the test strip, on the basis of each potential of the connecting lines 255, 256 immediately before the type judgement terminals 252, 253 are located at the set completion position 285, i.e., at the position 284, and selects the calibration curve information on the basis of the "calibration curve information selection change". The "calibration curve information selection change" is the potential change of the connecting lines 255, 256 while the type judgement terminals 252, 253 are moved from the positions 281 through 283. Accordingly, there are $2^4=16$ patterns of the calibration curve information selection change for selecting the calibration curve information and $2^2=4$ patterns of the potential change for selecting the information of the specific component in the fifth embodiment.

Based on the recognized pattern of the potential change, the CPU 258 selects and extracts from the memory part 259 the calibration curve information corresponding to the production lot of the set test strip 271 and the information of the specific component measurable by the test strip 271.

When the test strip 271 is set to the concentration measuring apparatus 251, the CPU 258 is turned into a measurable condition if the CPU 258 decides that the test strip 271 conforming to the specific component measurable by the measuring apparatus 251 is set based on the selected information indicative of the specific component, i.e., the information for the identification of the type of the test strip. And then the CPU 258 selects and extracts the calibration curve information corresponding to the production lot of the test strip 271. The concentration of, e.g., glucose in blood is measured via the positive electrode 102 and negative electrode 103 of the measuring apparatus 251 when the blood is dropped onto the reaction reagent of the set test strip 271. The CPU 258 calibrates the concentration with the use of the selected calibration curve information in operating the concentration of the specific component and make the result displayed. Since the measurement operation for the concentration is carried out essentially similar to the manner as is described in the first embodiment, the description thereof will be omitted here.

In contrast, if the test strip corresponding to a specific component not measurable by the measuring apparatus 251 is set, the CPU 258 is not turned to the measurable state and displays, for example, an error display.

In the above-described fifth embodiment, only when the test strip 271 having the reaction reagent measurable by the measuring apparatus 251 is set to the measuring apparatus 251, the measurement can be executed. Therefore, such an inconvenience can be prevented that a lactate test strip is set inadvertently to the measuring apparatus and a wrong result is obtained although glucose is to be measured. Moreover, when the test strip 271 for the specific component is set, the concentration can be calibrated with the use of the calibration curve information corresponding to the production lot of the test strip 271, thereby making it unnecessary for the user to pay attention to the production lot of the test strip and set the calibration test strip to select the calibration curve information. Thus, when a correct test strip, i.e. a test strip having the reaction reagent measurable by a measuring apparatus is set, the concentration of the component can be obtained without the calibration. The user is accordingly saved from the conventional trouble of using both the calibration test strip and the measurement test strip and then liberated from annoyance.

According to the fifth embodiment, as described hereinabove, the patterns in the appropriate test strip set change which is the potential change at the connecting lines 255, 256 are used to two kinds, i.e., the potential change pattern for the calibration curve information selection change and the potential change pattern for selecting the information indicative of the specific component. However, the present invention is not limited to this. For example, in the event that the specific component measurable by the measuring apparatus is already known and the test strip corresponding to the specific component is set at all times, the potential change pattern for selecting the information of the specific component is not required, and therefore, the patterns in the appropriate test strip set change can be totally utilized for the pattern of the calibration curve information selection change. To the contrary, the other kinds of the potential change may be added to the above to form three or more kinds of patterns.

The concentration measuring apparatus and test strip are not limited to the embodiment shown in FIGS. 19 and 20, for example, may be modified into forms shown in FIGS. 21 through 24 which will be now depicted below.

The potential change at the two connecting lines 255, 256 is used to select the calibration curve information and the specific component information in the above concentration measuring apparatus 251. On the other hand, according to a concentration measuring apparatus 301 of FIG. 21, a potential change at one connecting line 306 among three connecting lines 305–307 connected to three type judgement electrodes 302–304 is detected by a CPU 308 and this detected information is utilized at least for the selection of the calibration curve information. Both connecting lines 305, 307 are connected to each +5V power source via respective 10 kΩ resistors and, the connecting line 306 is earthed via a 100 kΩ resistor. A constitution of the measuring apparatus 301 in other points is not varied from that of the aforementioned measuring apparatus 251.

A fundamental concept related to formation of terminals on a test strip 321 to be set to the measuring apparatus 301 is similar to that of the test strip 271. However, a difference is that the test strip 321 is provided with one type judgement terminal 325 to the type judgement electrodes 302 and 303 although the test strip 271 has separate type judgement terminals 275 and 276 corresponding to the type judgement electrodes 252 and 253. Since the one type judgement terminal 325 is provided correspondingly to the type judgement electrodes 302 and 303, in the concentration measuring apparatus 301, the type judgement terminal 325 is adapted to be positioned at six points along the set direction I so as to obtain the above 64 patterns of the appropriate test strip set change, similar to the measuring apparatus 251. Needless to say, a count of the type judgement terminal 325 is not limited to the above six points and can be determined in accordance with a count of the patterns of the appropriate test strip set change.

The operation of the measuring apparatus 301 of the above constitution will be described.

At a start time point when the test strip 321 is started to be fitted to the measuring apparatus 301, the positive electrode 102, three type judgement electrodes 302–304, and negative electrode 103 are located at a position shown by a line 331. The positive electrode 102 is electrically connected to a positive terminal 323 of the test strip 321, the type judgement electrodes 302, 303 are electrically connected to the type judgement terminal 325, the type judgement electrode 304 is electrically connected to a type judgement terminal 327 and, the negative electrode 103 is electrically connected to a negative terminal 324. The type judgement terminal 327 of the test strip 321 generates the timing, similar to the type judgement terminal 277 of the test strip 271. In accordance with the movement of the test strip 321 in the set direction I, the type judgement terminal 327 generates the alternating potential change of the grounding potential and high level potential to the connecting line 307 connected to the type judgement electrode 304. In the measuring apparatus 301, the CPU 308 judges that the test strip 321 is normally set to the measuring apparatus 301 solely when the connecting line 307 becomes the high level potential three times after the start to completion of the setting of the test strip 321 and shows, e.g., an error display in other cases except the above.

When the type judgement electrodes 302 and 303 are electrically connected by the type judgement terminal 325, the source voltage is impressed to the connecting line 306 connected to the type judgement electrode 303 via the 10 kΩ resistor and connecting line 305, so that the connecting line 306 becomes the high level potential. When the test strip 321 moves further in the set direction I and if the type judgement terminal 325 is absent, e.g., as when the type judgement electrodes 302 and 303 are located at a position shown by a line 333, the type judgement electrodes 302 and 303 are not electrically connected with each other. In this case, the connecting line 306 is grounded via the 100 kΩ resistor and consequently turned to the low level potential. In the present example, in accordance with the movement of the test strip 321 from the start position to a set completion position where the positive electrode 102, three type judgement electrodes 302–304, and negative electrode 103 are on a line 337, the connecting line 306 shows the potential change from the high level potential→high level potential→low level potential→high level potential→high level potential→high level potential to the low level potential. Depending on a presence/absence of the type judgement terminal 325, the potential change can be given rise to the connecting line 306 while the test strip 321 is moved from the start position to the set completion position. The CPU 308 detects the potential change pattern at the connecting line 306, and then selects and extracts, e.g., the calibration curve information stored beforehand in a memory part 309 correspondingly to the potential change pattern of the connecting line 306. The measuring apparatus 301 operates in the same way in other points as the measuring apparatus 251, the description of which will be saved here.

Figure 23:
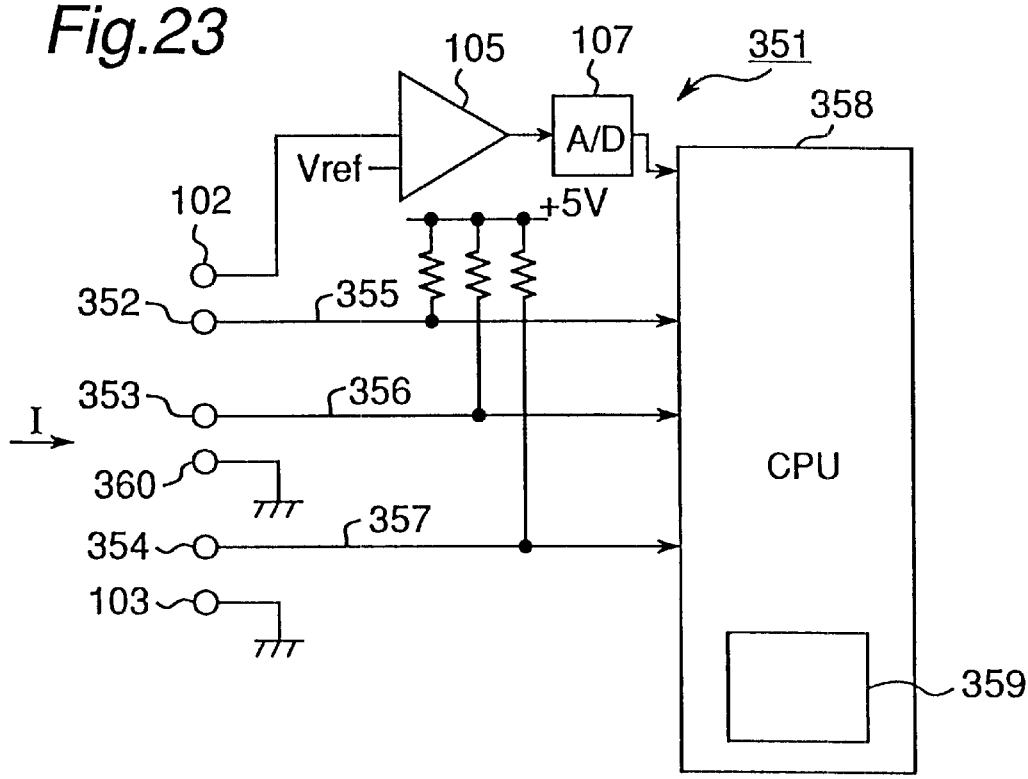
FIG. 23 is a structural diagram of a different modification of the concentration measuring apparatus of FIG. 19.
Figure 24:
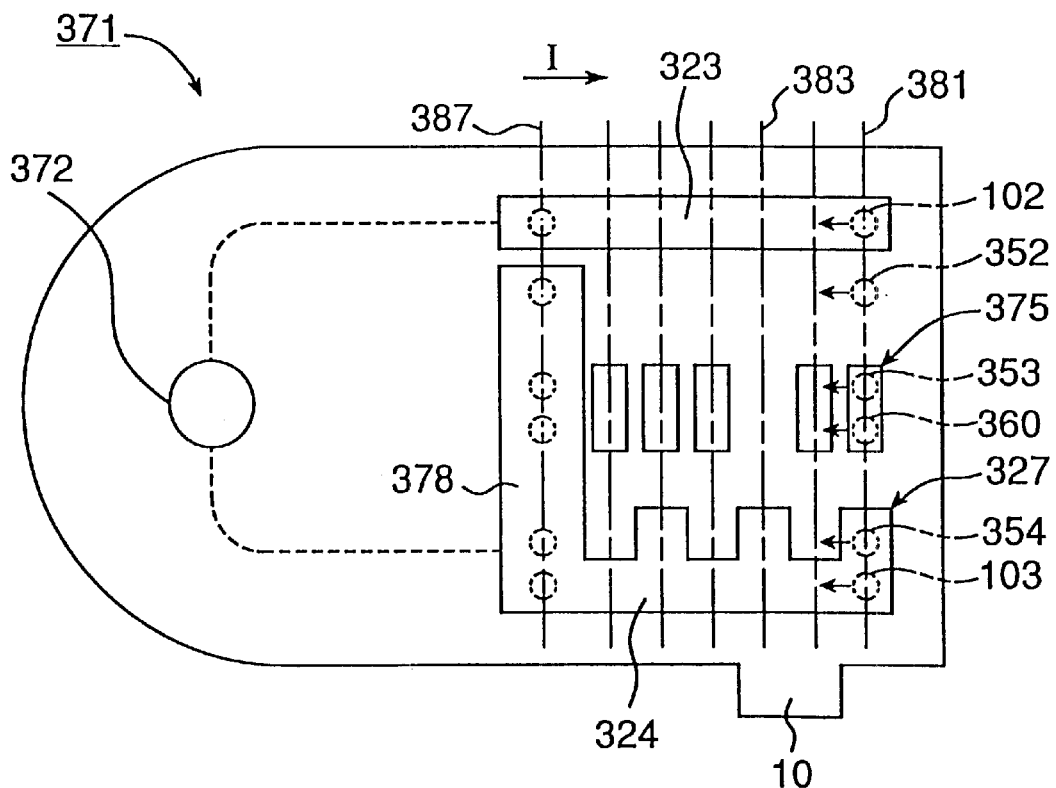
FIG. 24 is a plan view of a test strip to be set to the concentration measuring apparatus of FIG. 23.

Referring to FIG. 23, in a concentration measuring apparatus 351, a potential change at one connecting line 356 is detected, similar to the measuring apparatus 301, thereby to select, e.g., the calibration curve information. A constitution for generating the potential change to the connecting line 356 is different in comparison with the measuring apparatus 251. Specifically, the measuring apparatus 351 has three type judgement electrodes 352–354, connecting lines 355–357 connected to the type judgement electrodes 352–354, a CPU 358, and a memory part 359 storing the calibration curve information or the like. Each +5V power source is connected via respective resistors to the connecting lines 355–357. The measuring apparatus 351 is additionally provided with a grounding electrode 360 adjacent to the type judgement electrode 353 of the connecting line 356 generating a potential change detected by the CPU 358. When the CPU 358 detects that the type judgement electrode 352 is electrically connected to a set completion detection terminal 378 to be described later, the CPU 358 recognizes a set completion of a test strip 371 to the apparatus 351.

In the meantime, the test strip 371 to be set to the measuring apparatus 351 has the positive terminal 323, negative terminal 324, and type judgement terminal 375, etc., similar to the test strip 321. The test strip 371 also includes the set completion detection terminal 378 integrally formed with the negative terminal 324. The set completion detection terminal 378 detects when the test strip 371 is completely set to the measuring apparatus 351. The detection terminal 378 is formed to be electrically connected to the type judgement electrode 352 when the type judgement electrode 352 is located at the set completion position denoted by 387. The constitution of the test strip 371 in other points is the same as that of the test strip 321.

An operation of the thus-constituted measuring apparatus 351 will be described hereinbelow. Since the operation is fundamentally similar to that of the measuring apparatus 301, only a difference between the apparatus 351 and the apparatus 301 will be depicted.

That is, when the test strip 371 is started to be set to the measuring apparatus 351, the type judgement electrode 353 and grounding electrode 360 are located at a positon shown by a line 381 and electrically connected to the type judgement terminal 375. Since the electric connection of the type judgement electrode 353 is electrically connected to the grounding electrode 360 via the type judgement terminal 375, a potential change of the connecting line 356 detected by the CPU 358 becomes the grounding potential. When the test strip 371 is further inserted in the set direction I and the type judgement electrode 353 and grounding electrode 360 are located at a position shown by a line 383, since the test strip 371 has no type judgement terminal, the connecting line 356 becomes the high level potential of +5V.

According to the embodiment as is described hereinabove, with the movement of the test strip 371 before the positive electrode 102, three type judgement electrodes 352–354, grounding electrode 360, and negative electrode 103 reach the position shown by the line 387 after the test strip 371 is started to be inserted, the connecting line 356 shows the potential change from the grounding potential →grounding potential→high level potential→grounding potential→grounding potential→grounding potential to the grounding potential. Therefore, the connecting line 356 undergoes the potential change in accordance with the movement of the test strip 371 after the start to the completion of the setting, depending on presence/absence of the type judgement terminal 375. The CPU 358 detects the potential change pattern of the connecting line 356, and then selects and extracts, e.g., the calibration curve information stored in the memory part 359 beforehand correspondingly to the potential change pattern of the connecting line 356. The measuring apparatus 351 operates in the same manner in other points as the measuring apparatus 251 described earlier, and therefore the description thereof will be omitted.

A method for forming the positive terminal, type judgement terminals, negative terminal, and set completion detection terminal formed in the test strip of the fifth embodiment, particularly, a method for forming the type judgement terminals will be explained below.

As described before, the test strip inevitably includes the measurement error for every production lot and the large factor for the measurement error is the production error of the enzyme in the reaction reagent. Thus, the method for forming the judge elements to be described hereinbelow is a method to form the judge elements based on the production error of the enzyme. The test strip 271 is taken as an example in the following description, and the following description is directed to a case of forming the calibration curve information selection pattern to the type judgement terminals 275–277 of the test strip.

There are generally two methods for forming the positive terminal, type judgement terminals, etc. According to a first method, after the production error of the reaction reagent, particularly, of the enzyme is confirmed, the type judgement terminal is formed so that at least the calibration curve information selection change is brought about to the connecting line. According to a second method, a type judgement terminal without a pattern is formed preliminarily along the set direction I and, after the production error of especially the enzyme is confirmed, an insulating substance is applied onto the type judgement terminal without the pattern so that at least the calibration curve information selection change is brought about to the connecting line.

Figure 25:
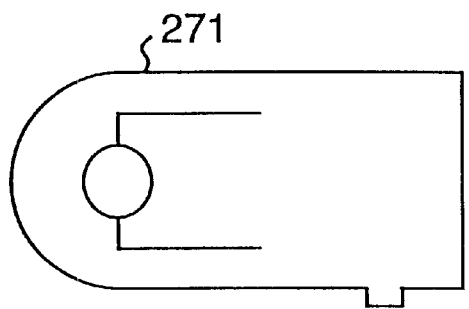
FIG. 25 is a diagram explanatory of a first formation method for forming terminals in each test strip of FIGS. 20, 22, and 24.
Figure 26:
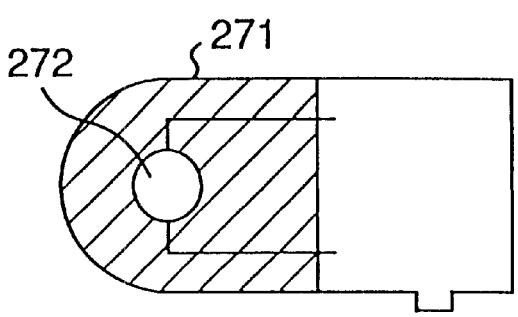
FIG. 26 is a diagram explanatory of the first formation method for forming terminals in each test strip of FIGS. 20, 22, and 24.
Figure 27:
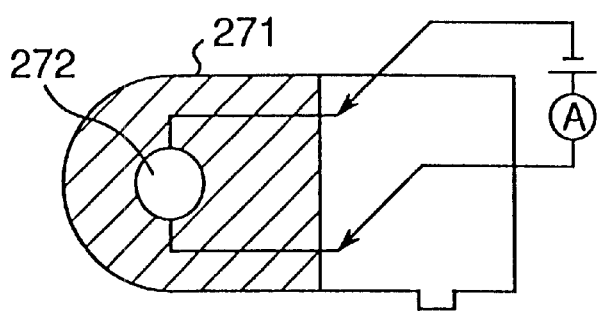
FIG. 27 is a diagram explanatory of the first formation method for forming terminals in each test strip of FIGS. 20, 22, and 24.
Figure 28:
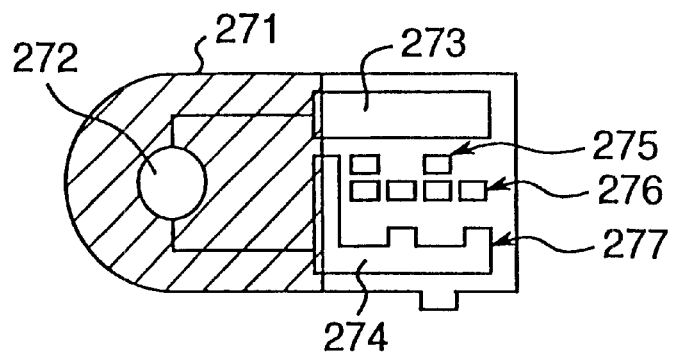
FIG. 28 is a diagram explanatory of the first formation method for forming terminals in each test strip of FIGS. 20, 22, and 24.

The aforementioned first method will be described with references to FIGS. 25 through 28. As shown in FIG. 25, the measuring electrode, counter electrode, and connecting lines connected to these electrodes are formed on the base material of a sample test strip 271 to determine the calibration curve information. An insulating layer is formed with an insulating paste or the like except a part of the measuring electrode and counter electrode, as indicated by slanted lines in FIG. 26, and thereafter the reaction reagent 272 is applied on the measuring electrode and counter electrode. The slanted lines in FIGS. 26–28 are not a hatching representing a cross section. Then, in FIG. 27, a standard solution containing a specific component which reacts to the reaction reagent 272 and a concentration of which is known is dropped to the reaction reagent 272, and a voltage is applied to a part of the reaction reagent 272. Then a concentration, i.e., a current value is measured. A measurement error of the reaction reagent 272 is obtained on the basis of the measured concentration and the known concentration. In FIG. 28, type judgement terminals 275, 276 and positive terminal 273, etc. are formed of conductive material so that the calibration curve information selection change corresponding to the calibration curve information compensating for the above measurement error is brought about with the type judgement terminals 275, 276 and positive terminal 273, etc.

In the foregoing description, the test strip is the sample for determining the calibration curve information. In a case of the test strip 271 for sale to which a reaction reagent including an enzyme of the same production lot as the enzyme of the reaction reagent applied to the sample element is applied, a type of the conductive material forming the type judgement terminal 275, etc. should be selected in accordance with an application timing of the reaction reagent onto the base material. Namely, in general, the enzyme included in the reaction reagent 272 is weak to heat and an activity of the enzyme is decreased or the enzyme becomes inactive once a temperature not lower than about 50° C. acts the enzyme, whereby the test strip 271 is inoperative. Thus, in the case where the test strip 271 is produced after the calibration curve information corresponding to the production lot is determined, and if the reaction reagent 272 is applied onto the base material before the type judgement terminal 275, etc. are formed, a conductive material of a type cured at normal temperatures should be used for the type judgement terminal 275, etc., as in FIG. 28. The conductive material of the above type is, for example, a conductive adhesive containing silver and an epoxy resin binder such as "ELECTRODAG5820" (trade name by Acheson (Japan) Ltd.) or a conductive adhesive containing nickel and a thermoplastic binder such as "SS24306" (trade name by Acheson (Japan) Ltd.), etc.

Meanwhile, when the reaction reagent 272 is applied on the base material after the type judgement terminal 275, etc. are formed, the conductive material of the above-described type, i.e., cured at normal temperatures is not necessary and a conventionally used thermosetting conductive material requiring heating at approximately 130–150° C. can be employed.

The second method will be described with reference to FIGS. 29–32.

Figure 29:
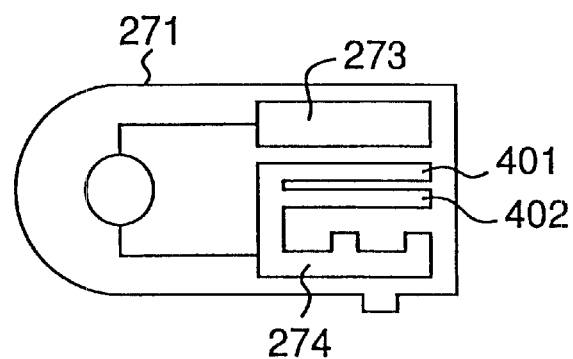
FIG. 29 is a diagram explanatory of a second formation method for forming terminals in each test strip of FIGS. 20, 22, and 24.
Figure 30:
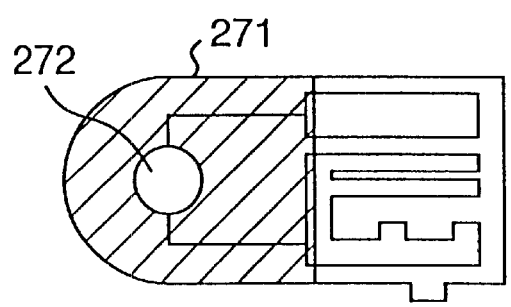
FIG. 30 is a diagram explanatory of the second formation method for forming terminals in each test strip of FIGS. 20, 22, and 24.
Figure 31:
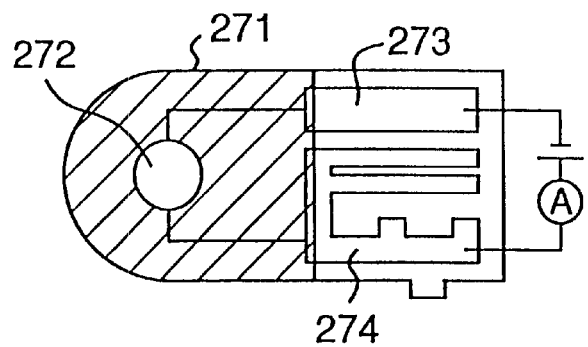
FIG. 31 is a diagram explanatory of the second formation method for forming terminals in each test strip of FIGS. 20, 22, and 24.
Figure 32:
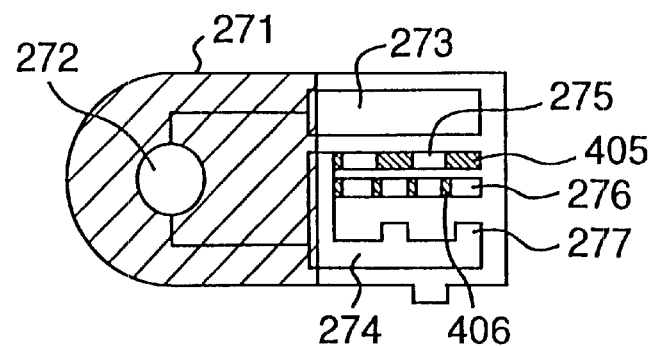
FIG. 32 is a diagram explanatory of the second formation method for forming terminals in each test strip of FIGS. 20, 22, and 24.

In FIG. 29, on the base material of the sample test strip 271 used for determining the calibration curve information are formed the measuring electrode, the counter electrode, the connecting lines connected to these electrodes, the positive terminal 273, the negative terminal 274, the set completion detection terminal 278, and type judgement terminals 401, 402 without the pattern. Similar to the description with reference to FIG. 26, after an insulating layer is formed except the part of the measuring electrode and counter electrode, the reaction reagent 272 is applied, as indicated by slanted lines in FIG. 30. The slanted lines in FIGS. 30–32 are not a hatching to express cross sections. In FIG. 31, the standard solution is dropped to the reaction reagent 272, and a voltage is applied to the part of the reaction reagent 272 via the positive terminal 273 and negative terminal 274. Then, a concentration of the standard solution, i.e., a current is measured. Based on the measured concentration and known concentration, a measurement error of the reaction reagent 272 is obtained. In FIG. 32, then, insulating pastes 405, 406, etc. are applied as indicated by slanted lines onto the type judgement terminals 401, 402 without the pattern so that the calibration curve information capable of compensating for the above measurement error can be selected, thereby to form a pattern for selecting the calibration curve information and obtain type judgement terminals 275, 276. As a way to form the pattern for selecting the calibration curve information to the type judgement terminals 401, 402 without the pattern, cutting or the like process may be performed to the type judgement terminals 401, 402, in place of applying the insulating pastes 405, 406 of the type cured at normal temperatures.

The insulating pastes 405, 406 of the above type are, e.g., an insulating ink containing a polyurethane PV series resin binder such as "JEF-226C" (trade name by Acheson (Japan) Ltd.) or an insulating ink containing a polyester resin binder such as "JEH-116G" (trade name by Acheson (Japan) Ltd.), etc.

As mentioned earlier, the insulating paste of the thermosetting type can be used depending on the application timing of the reaction reagent 272 to the test strip 271.

According to the second method as above, since the positive terminal 273 and negative terminal 274 are used when the concentration of the standard solution is measured as in FIG. 31, the concentration can be measured with the production error of the conductive carbon paste as the material for the positive terminal 273 and negative terminal 274 included, unlike the first method. Therefore, the concentration of the specific component can be measured with higher accuracy than by the first method.

The entire disclosure of Japanese Patent Application No.9-195866 filed on Jul. 22, 1997, including specification, claims, drawings, and summary are incorporated herein by reference in its entirety.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A concentration measuring apparatus and a test strip which is applied thereto, the test strip including on a base material a reaction reagent for reacting with a liquid test sample, a positive terminal, and a negative terminal, the terminals electrically detecting a concentration of a specific component in the liquid test sample based on the reaction of the reaction reagent, the concentration measuring apparatus comprising a positive electrode and a negative electrode to be electrically connected respectively to the positive terminal and the negative terminal of the test strip, thereby measuring the concentration of the specific component in the liquid test sample via the positive electrode and the negative electrode, the concentration measuring apparatus further comprising a reagent identifying electrode for identifying a type of the reaction reagent formed on the test strip which measures the concentration of a sample applied to the concentration measuring apparatus, with the reagent identifying electrode being provided separately from the positive electrode and negative electrode;

a first identification device for feeding information corresponding to the test strip based on the reagent identifying electrode being connected with the positive electrode only when the test strip is applied to the concentration measuring apparatus, and a second identification device for identifying the test strip based on the information fed from the first identification device.

2. The concentration measuring apparatus according to claim 1, which comprises a reagent identifying terminal on the test strip which is electrically connected to the reagent identifying electrode and positive electrode, thereby letting the first identification device of the concentration measuring apparatus send out the information corresponding to the test strip.

3. The concentration measuring apparatus according to claim 1, further comprising a reagent detector which determines that the test strip corresponds to the concentration measuring apparatus.

4. The concentration measuring apparatus according to claim 1, further comprising a reagent detector which determines that the test strip having the reaction reagent which is to react to the specific component in the liquid test sample corresponds to the concentration measuring apparatus.

5. A concentration measuring apparatus and a test strip which is applied thereto, the test strip including on a base material a reaction reagent for reacting with a liquid test sample, a positive terminal, and a negative terminal, the terminals electrically detecting a concentration of a specific component in the liquid test sample based on the reaction of the reaction reagent, the concentration measuring apparatus comprising a positive electrode and a negative electrode to be electrically connected respectively to the positive terminal and the negative terminal of the test strip, thereby measuring the concentration of the specific component in the liquid test sample via the positive electrode and the negative electrode, the concentration measuring apparatus further comprising a reagent identifying electrode for identifying a type of the reaction reagent formed on the test strip which measures the concentration of a sample applied to the concentration measuring apparatus, with the reagent identifying electrode being provided separately from the positive electrode and negative electrode;

switches for connecting and disconnecting the reagent identifying electrode and positive electrode to an identification device, and for connecting and disconnecting the reagent identifying electrode and negative electrode to the identification device, the identification device for identifying that the test strip is applied to the concentration measuring apparatus on the basis of information obtained from a detecting part of the positive electrode after operating said switches.

6. The concentration measuring apparatus according to claim 5, further comprising a reagent detector which determines that the test strip corresponds to the concentration measuring apparatus.

7. The concentration measuring apparatus according to claim 5, further comprising a reagent detector which determines that the test strip having the reaction reagent which is to react to the specific component in the liquid test sample corresponds to the concentration measuring apparatus.

8. A concentration measuring apparatus and a test strip which is applied thereto, the test strip including on a base material a reaction reagent for reacting with a liquid test sample, a positive terminal, and a negative terminal, the terminals electrically detecting a concentration of a specific component in the liquid test sample based on the reaction of the reaction reagent, the concentration measuring apparatus comprising a positive electrode and a negative electrode to be electrically connected respectively to the positive terminal and the negative terminal of the test strip, thereby measuring the concentration of the specific component in the liquid test sample via the positive electrode and the negative electrode, the concentration measuring apparatus further comprising a reagent identifying electrode for identifying a type of the reaction reagent formed on the test strip which measures the concentration of a sample applied to the concentration measuring apparatus, with the reagent identifying electrode being provided separately from the positive electrode and negative electrode;

a potential judge device connected to the reagent identifying electrode which judges whether or not the reagent identifying electrode has a strip set potential corresponding to the concentration measuring apparatus generated at the reagent identifying electrode when the test strip for the liquid test sample is applied to the concentration measuring apparatus.

9. The concentration measuring apparatus according to claim 8, which comprises a reagent identifying terminal on the test strip which is electrically connected to the reagent identifying electrode for letting the potential judge device judge that the potential at the reagent identifying electrode is at a test strip set potential corresponding to the concentration measuring apparatus.

10. The concentration measuring apparatus according to claim 8, further comprising a reagent detector which determines that the test strip corresponds to the concentration measuring apparatus.

11. The concentration measuring apparatus according to claim 8, further comprising a reagent detector which determines that the test strip having the reaction reagent which is to react to the specific component in the liquid test sample corresponds to the concentration measuring apparatus.

12. A concentration measuring apparatus and a test strip which is applied thereto, the test strip including on a base material a reaction reagent for reacting with a liquid test sample, a positive terminal, and a negative terminal, the terminals electrically detecting a concentration of a specific component in the liquid test sample based on the reaction of the reaction reagent, the concentration measuring apparatus comprising a positive electrode and a negative electrode to be electrically connected respectively to the positive terminal and the negative terminal of the test strip, thereby measuring the concentration of the specific component in the liquid test sample via the positive electrode and the negative electrode, the concentration measuring apparatus further comprising a reagent identifying electrode for identifying a type of the reaction reagent formed on the test strip which measures the concentration of a sample applied to the concentration measuring apparatus, with the reagent identifying electrode being provided separately from the positive electrode and negative electrode;

the reagent identifying electrode comprises at least two high level electrodes set at a high level potential, and a grounding electrode set at a low level potential, so that at least one of combinations of potentials at the two high level electrodes and the grounding electrode corresponds to the test strip set potential corresponding to the concentration measuring apparatus.

13. The concentration measuring apparatus according to claim 12, which comprises at least two reagent identifying terminals on the test strip to be electrically connected at least to the three reagent identifying electrodes, enabling the potential judge device to judge the test strip set potential through a combination of connections of the reagent identifying electrodes and the reagent identifying terminals.

14. The corresponding measuring apparatus according to claim 13, wherein the reagent identifying terminal enabling the potential judge device to judge the test strip set potential comprises a second terminal for electrically connecting one of the high level electrodes and the grounding electrode, and a first terminal to be electrically connected to the remaining high level electrode.

15. A concentration measuring apparatus and a test strip which is applied thereto, the test strip including on a base material a reaction reagent for reacting with a liquid test sample, a positive terminal, and a negative terminal, the terminals electrically detecting a concentration of a specific component in the liquid test sample based on the reaction of the reaction reagent, the concentration measuring apparatus comprising a positive electrode and a negative electrode to be electrically connected respectively to the positive terminal and the negative terminal of the test strip, thereby measuring the concentration of the specific component in the liquid test sample via the positive electrode and the negative electrode, the concentration measuring apparatus furthercomprising a reagent identifying electrode for identifying a type of the reaction reagent formed on the test strip which measures the concentration of a sample applied to the concentration measuring apparatus, with the reagent identifying electrode being provided separately from the positive electrode and negative electrode;

a change judge device connected to the reagent identifying electrode which judges whether or not a potential change at the reagent identifying electrode corresponds to a test strip set change corresponding to the concentration measuring apparatus which is a change generated at the reagent identifying electrode when the test strip is applied to the concentration measuring apparatus.

16. The concentration measuring apparatus according to claim 15, wherein the reagent identifying electrode is set at the high level potential.

17. The concentration measuring apparatus according to claim 16, which comprises a reagent identifying terminal on the test strip to be electrically connected to the reagent identifying electrode and letting the change judge device judge that the potential change at the reagent identifying electrode is the test strip set change.

18. The concentration measuring apparatus according to claim 17, wherein the reagent identifying terminal is electrically connected to the negative terminal, is electrically connected to the reagent identifying electrode of the concentration measuring apparatus when the test strip is first applied to the concentration measuring apparatus, and brings about the appropriate test strip set change to the reagent identifying electrode from the low level to high level after the test strip is first applied to the concentration measuring apparatus before being completely applied.

19. The concentration measuring apparatus according to claim 16, wherein the change judge device stores a plurality of calibration curve information for compensating for an error in concentration measurement of the specific component in the liquid test sample, selects a required calibration curve information among the plurality of calibration curve information on the basis of a calibration curve information selection change included in the appropriate test strip set change at the reagent identifying electrode as well as judges a type of the test strip on the basis of the appropriate test strip set change at the reagent identifying electrode, and compensates for the error based on the selected calibration curve information;

wherein the error in concentration measurement results from a reaction error of the liquid test sample caused by a production error for every production lot of the reaction reagent of the test strip applied to the concentration measuring apparatus.

20. The concentration measuring apparatus according to claim 19, wherein the change judge device stores the plurality of calibration curve information for every specific component corresponding to the type of the set test strip.

21. The concentration measuring apparatus according to claim 20, wherein the reagent identifying electrode includes:

a first electrode which exhibits the appropriate test strip set change from the high level to low level and from the low level to the high level after the test strip is started to be applied to the concentration measuring apparatus before completely applied, and the calibration curve information selection change; and a second electrode which alternatively generates the high level potential and low level potential synchronously with the potential change at the first electrode so as to detect a timing of the potential change of the first electrode after the test strip is started to be applied to the concentration measuring apparatus before completely applied.

22. The concentration measuring apparatus according to claim 19, wherein the reagent identifying electrode includes:

a first electrode which exhibits the appropriate test strip set change from the high level to low level and from the low level to the high level after the test strip is started to be applied to the concentration measuring apparatus before completely applied, and the calibration curve information selection change; and a second electrode which alternatively generates the high level potential and low level potential synchronously with the potential change at the first electrode so as to detect a timing of the potential change of the first electrode after the test strip is started to be applied to the concentration measuring apparatus before completely applied wherein the error in concentration measurement results from a reaction error of the liquid test sample caused by a production error for every production lot of the reaction reagent of the test strip applied to the concentration measuring apparatus.

23. The concentration measuring apparatus according to claim 22, further comprising a reagent detector which determines that the test strip corresponds to the concentration measuring apparatus.

24. The concentration measuring apparatus according to claim 22, further comprising a reagent detector which determines that the test strip having the reaction reagent which is to react to the specific component in the liquid test sample corresponds to the concentration measuring apparatus.

25. The concentration measuring apparatus according to claim 19, which has a reagent identifying terminal to be electrically connected to the reagent identifying electrode and letting the change judge device judge that the potential change at the reagent identifying electrode is the appropriate test strip set change for judging the type of the test strip and also letting the change judge device detect the calibration curve selection information change for selecting the required calibration curve information among the plurality of calibration curve information.

26. The concentration measuring according to claim 25, wherein the reagent identifying terminal has:

a potential change part which makes a first electrode included in the reagent identifying electrode of the concentration measuring apparatus represent the appropriate test strip set change and the calibration curve information selection change from the high level to low level and from the low level to high level after the test strip is first applied to the concentration measuring apparatus before being completely applied; and a timing generation part which makes a second electrode included in the reagent identifying electrode of the concentration measuring apparatus alternately generate the high level potential and the low level potential synchronously with the potential change brought about to the first electrode after the test strip is first applied to the concentration measuring apparatus before being completely applied.

27. The concentration measuring apparatus according to claim 26, which includes a set completion detection terminal to be electrically connected to the positive electrode or negative electrode of the concentration measuring apparatus when the test strip is completely applied to the concentration measuring apparatus, so that the set completion detection terminal makes the concentration measuring apparatus detect the completion of the application.

28. The concentration measuring apparatus according to claim 26, wherein the set completion detection part and the timing generation part are electrically connected to the negative terminal of the test strip.

29. The method for manufacturing the concentration measuring apparatus according to claim 26, which comprises:

applying the reaction reagent on the base material of the test strip;

depositing a standard solution having the specific component of which a concentration is known on the applied reaction reagent;

selecting the calibration curve information compensating for an error between a detected concentration based on the reaction and the known concentration of the specific component; and forming the reagent identifying terminal so that the calibration curve information selection change indicating at least the selected calibration curve information is generated at the reagent identifying terminal.

30. The manufacture method according to claim 29, whereby the reagent identifying terminal is formed on the base material of the test strip after the calibration curve information is selected so that the reagent identifying terminal includes an indication of the selected calibration curve information.

31. The manufacture method according to claim 29, whereby the reagent identifying terminal is formed in a process of preliminary forming a patternless reagent identifying terminal not showing the calibration curve information selection change on the base material of the test strip, and then forming a calibration curve information selection change pattern to the patternless reagent identifying terminal after the calibration curve information is selected so that the reagent identifying terminal includes the selected calibration curve information.

32. The method for manufacturing the concentration measuring apparatus according to claim 25, which comprises:

applying the reaction reagent on the base material of the test strip;

depositing a standard solution having the specific component of which a concentration is known on the applied reaction reagent;

selecting the calibration curve information compensating for an error between a detected concentration based on the reaction and the known concentration of the specific component; and forming the reagent identifying terminal so that the calibration curve information selection change indicating at least the selected calibration curve information is generated at the reagent identifying terminal.

33. The manufacture method according to claim 32, whereby the reagent identifying terminal is formed on the base material of the test strip after the calibration curve information is selected so that the reagent identifying terminal includes an indication of the selected calibration curve information.

34. The manufacture method according to claim 32, whereby the reagent identifying terminal is formed in a process of preliminarily forming a patternless reagent identifying terminal not showing the calibration curve information selection change on the base material of the test strip, and then forming a calibration curve information selection change pattern to the patternless reagent identifying terminal after the calibration curve information is selected so that the reagent identifying terminal includes the selected calibration curve information.

35. The concentration measuring apparatus according to claim 19, further comprising a reagent detector which determines that the test strip corresponds to the concentration measuring apparatus.

36. The concentration measuring apparatus according to claim 19, further comprising a reagent detector which determines that the test strip having the reaction reagent which is to react to the specific component in the liquid test sample corresponds to the concentration measuring apparatus.

37. The concentration measuring apparatus according to claim 15, which comprises a reagent identifying terminal on the test strip to be electrically connected to the reagent identifying electrode and letting the change judge device judge that the potential change at the reagent identifying electrode corresponds to the test strip set change.

38. The concentration measuring apparatus according to claim 37, wherein the reagent identifying terminal is electrically connected to the positive terminal or negative terminal, is electrically connected to the reagent identifying electrode of the concentration measuring apparatus either when the test strip is first applied to the concentration measuring apparatus or when the test strip is completely applied to the concentration measuring apparatus, and brings about the test strip set change to the reagent identifying electrode from the high level to low level or from the low level to high level after the test strip is first applied to the concentration measuring apparatus before being completely applied.

39. The concentration measuring apparatus according to claim 15, wherein the change judge device stores a plurality of calibration curve information for compensating for an error in concentration measurement of the specific component in the liquid test sample, detects a calibration curve information selection change at the reagent identifying electrode so as to select a required calibration curve information among the plurality of calibration curve information in place of judging the presence/absence of the appropriate test strip set change at the reagent identifying electrode when the concentration measuring apparatus can measure the concentration of the only one specific component and the test strip having a reaction reagent which is to react to the specific component and capable of measuring the concentration of the specific component by the concentration measuring apparatus is set to the concentration measuring apparatus, and compensates for the error based on the calibration curve information selected in accordance with the detected calibration curve information selection change;

wherein the error in concentration measurement results from a reaction error of the liquid test sample caused by a production error for every production lot of the reaction reagent of the test strip applied to the concentration measuring apparatus.

40. The concentration measuring apparatus according to claim 39, which has a reagent identifying terminal to be electrically connected to the reagent identifying electrode and letting the change judge device detect the calibration curve information selection change for selecting the required calibration curve information among the plurality of calibration curve information on the basis of the potential at the reagent identifying electrode.

41. The concentration measuring apparatus according to claim 40, wherein the reagent identifying terminal comprises:

a potential change part which makes a first electrode included in the reagent identifying electrode of the concentration measuring apparatus represent the calibration curve information selection change from the high level potential to low level potential and from the low level potential to high level potential after the test strip is first applied to the concentration measuring apparatus before being completely applied; and a timing generation part which makes a second electrode included in the reagent identifying electrode of the concentration measuring apparatus alternately generate the high level potential and low level potential synchronously with the potential change brought about to the first electrode after the test strip is first applied to the concentration measuring apparatus before being completely applied.

42. The concentration measuring apparatus according to claim 41, which includes a set completion detection terminal to be electrically connected to the positive electrode or the negative electrode of the concentration measuring apparatus when the test strip is completely applied to the concentration measuring apparatus, so that the completion of the applying is detected with the concentration measuring apparatus.

43. The concentration measuring apparatus according to claim 41, wherein the set completion detection part and the timing generation part are electrically connected to the negative terminal of the test strip.

44. The method for manufacturing the concentration measuring apparatus according to claim 41, which comprises:
  applying the reaction reagent on the base material of the test strip;
  depositing a standard solution having the specific component of which a concentration is known on the applied reaction reagent;
  selecting the calibration curve information compensating for an error between a detected concentration based on the reaction and the known concentration of the specific component; and
  forming the reagent identifying terminal so that the calibration curve information selection change indicating at least the selected calibration curve information is generated at the reagent identifying terminal.

45. The manufacture method according to claim 44, whereby the reagent identifying terminal is formed on the base material of the test strip after the calibration curve information is selected so that the reagent identifying terminal includes an indication of the selected calibration curve information terminal.

46. The manufacture method according to claim 44, whereby the reagent identifying terminal is formed in a process of preliminary forming a patternless reagent identifying terminal not showing the calibration curve information selection change on the base material of the test strip, and then forming a calibration curve information selection change pattern to the patternless reagent identifying terminal after the calibration curve information is selected so that the reagent identifying terminal includes the selected calibration curve information.

47. The method for manufacturing the concentration measuring apparatus according to claim 40, comprises:
  applying the reaction reagent on the base material of the test strip;
  depositing a standard solution having the specific component of which a concentration is known on the applied reaction reagent;
  selecting the calibration curve information compensating for an error between a detected concentration based on the reaction and the known concentration of the specific component; and
  forming the reagent identifying terminal so that the calibration curve information selection change indicating at least the selected calibration curve information is generated at the reagent identifying terminal.

48. The manufacture method according to claim 47, whereby the reagent identifying terminal is formed on the base material of the test strip after the calibration curve information is selected so that the reagent identifying terminal includes an indication of the selected calibration curve information.

49. The manufacture method according to claim 47, whereby the reagent identifying terminal is formed in a process of preliminary forming a patternless reagent identifying terminal not showing the calibration curve information selection change on the base material of the test strip, and then forming a calibration curve information selection pattern to the patternless reagent identifying terminal after the calibration curve information is selected so that the reagent identifying terminal includes an indication of the selected calibration curve information.

50. The concentration measuring apparatus according to claim 15, further comprising a reagent detector which determines that the test strip corresponds to the concentration measuring apparatus.

51. The concentration measuring apparatus according to claim 15, further comprising a reagent detector which determines that the test strip having the reaction reagent which is to react to the specific component in the liquid test sample corresponds to the concentration measuring apparatus.

52. A biosensor system comprising:
  a first concentration measuring apparatus comprising the concentration measuring apparatus to which a test strip is applied, the test strip including on a base material a reaction reagent reacting with a liquid test sample, a positive terminal, and a negative terminal, the terminals electrically detecting a concentration of a specific component in the liquid test sample based on the reaction of the reaction reagent, the concentration measuring apparatus comprising a positive electrode and a negative electrode to be electrically connected respectively to the positive terminal and the negative terminal of the test strip, thereby measuring the concentration of the specific component in the liquid test sample via the positive electrode and the negative electrode,
  the concentration measuring apparatus further comprising a reagent identifying electrode for identifying a type of the reaction reagent formed on the test strip which measures the concentration of a sample applied to the concentration measuring apparatus, with the reagent identifying electrode being provided separately from the positive electrode and negative electrode, and
  which further comprises a first identification device for feeding information corresponding to the test strip based on the reagent identifying electrode being connected with the positive electrode only when the test strip is applied to the concentration measuring apparatus, and
  a second identification device for identifying the test strip based on the information fed from the first identification device and wherein the positive electrode, the reagent identifying electrode, and the negative electrode are arranged in this order in a transverse direction of a test strip;
  a first test strip, including on a base material a reaction reagent for reacting with a liquid test sample, a positive terminal, and a negative terminal, the terminals electrically detecting a concentration of a specific component in the liquid test sample based on the reaction of the reaction reagent, a reagent identifying terminal which is electrically connected to the reagent identifying electrode and positive electrode, applied to the first concentration measuring apparatus, which includes first terminals to be electrically connected to the positive electrode and the reagent identifying electrode, and a second terminal to be electrically connected to the negative electrode;

a second concentration measuring apparatus comprising the concentration measuring apparatus as used for the first concentration measuring apparatus wherein the positive electrode, the negative electrode, and the reagent identifying electrode are arranged in this order in the transverse direction; and a second test strip, including on a base material a reaction reagent for reacting with a liquid test sample, a positive terminal, and a negative terminal, the terminals electrically detecting a concentration of a specific component in the liquid test sample based on the reaction of the reaction reagent, a reagent identifying terminal which is electrically connected to the reagent identifying electrode and positive electrode, applied to the second concentration measuring apparatus which includes a first terminal to be electrically connected to the positive electrode and reagent identifying electrode and a second terminal to be electrically connected to the negative electrode, said biosensor system so constituted that a concentration of the specific component cannot be measured if the first test strip is applied to the second concentration measuring apparatus, and if the second test strip is applied to the first concentration measuring apparatus.

* * * * *